US009523093B2

(12) United States Patent
Davidson et al.

(10) Patent No.: US 9,523,093 B2
(45) Date of Patent: Dec. 20, 2016

(54) HUNTINGTON'S DISEASE THERAPEUTIC COMPOUNDS

(71) Applicant: University of Iowa Research Foundation, Iowa City, IA (US)

(72) Inventors: Beverly L. Davidson, Iowa City, IA (US); Alejandro Mas Monteys, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 14/717,795

(22) Filed: May 20, 2015

(65) Prior Publication Data

US 2016/0060624 A1  Mar. 3, 2016

Related U.S. Application Data

(60) Provisional application No. 62/000,895, filed on May 20, 2014.

(51) Int. Cl.
| | |
|---|---|
| C12N 15/11 | (2006.01) |
| C12N 15/113 | (2010.01) |
| A61K 9/00 | (2006.01) |
| A61K 31/7088 | (2006.01) |

(52) U.S. Cl.
CPC .......... *C12N 15/113* (2013.01); *A61K 9/0085* (2013.01); *A61K 31/7088* (2013.01); *C12N 2310/14* (2013.01); *C12N 2310/141* (2013.01); *C12N 2320/30* (2013.01); *C12N 2320/32* (2013.01); *C12N 2330/51* (2013.01)

(58) Field of Classification Search
None
See application file for complete search history.

(56) References Cited

U.S. PATENT DOCUMENTS

| | | | |
|---|---|---|---|
| 4,962,091 A | 10/1990 | Eppstein et al. | |
| 5,139,941 A | 8/1992 | Muzyczka et al. | |
| 5,173,414 A | 12/1992 | Lebkowski et al. | |
| 5,350,674 A | 9/1994 | Boenisch et al. | |
| 5,585,362 A | 12/1996 | Wilson et al. | |
| 5,720,720 A | 2/1998 | Laske et al. | |
| 7,232,806 B2 | 6/2007 | Tuschl et al. | |
| 7,320,965 B2 | 1/2008 | Sah et al. | |
| 7,902,352 B2 | 3/2011 | Kaemmerer et al. | |
| 8,227,592 B2 | 7/2012 | Harper et al. | |
| 8,258,286 B2 | 9/2012 | Davidson | |
| 8,329,890 B2 | 12/2012 | Davidson et al. | |
| 8,481,710 B2 | 7/2013 | Davidson et al. | |
| 8,487,088 B2 | 7/2013 | Davidson et al. | |
| 8,524,879 B2 | 9/2013 | Davidson et al. | |
| 8,524,881 B2 | 9/2013 | Davidson | |
| 8,691,567 B2 | 4/2014 | Harper et al. | |
| 8,779,116 B2 | 7/2014 | Davidson et al. | |
| 9,181,544 B2 | 11/2015 | Davidson et al. | |
| 2002/0114780 A1 | 8/2002 | Bankiewicz et al. | |
| 2002/0141980 A1 | 10/2002 | Bankiewicz et al. | |
| 2002/0187127 A1 | 12/2002 | Bankiewicz | |
| 2004/0023390 A1 | 2/2004 | Davidson et al. | |
| 2004/0162255 A1 | 8/2004 | Kaemmerer et al. | |
| 2004/0241854 A1 | 12/2004 | Davidson et al. | |
| 2005/0042646 A1 | 2/2005 | Davidson et al. | |
| 2005/0106731 A1 | 5/2005 | Davidson et al. | |
| 2005/0255086 A1 | 11/2005 | Davidson et al. | |
| 2006/0009408 A1 | 1/2006 | Davidson et al. | |
| 2006/0130176 A1 | 6/2006 | Reyes-Taboada et al. | |
| 2006/0257912 A1 | 11/2006 | Kaemmerer et al. | |
| 2008/0039418 A1 | 2/2008 | Freier | |
| 2008/0176812 A1 | 7/2008 | Davidson et al. | |
| 2008/0274989 A1 | 11/2008 | Davidson et al. | |
| 2009/0004668 A1 | 1/2009 | Chen et al. | |
| 2009/0036395 A1 | 2/2009 | Davidson et al. | |
| 2009/0105169 A1 | 4/2009 | Davidson et al. | |
| 2009/0130751 A1 | 5/2009 | Davidson et al. | |
| 2010/0008981 A1 | 1/2010 | Kaemmerer et al. | |
| 2010/0144026 A1 | 6/2010 | Davidson et al. | |
| 2010/0190243 A1 | 7/2010 | Davidson et al. | |
| 2010/0291673 A1 | 11/2010 | Harper et al. | |
| 2010/0325746 A9 | 12/2010 | Kaemmerer et al. | |
| 2011/0111491 A1 | 5/2011 | Davidson et al. | |
| 2011/0212520 A1 | 9/2011 | Davidson et al. | |
| 2011/0244561 A1 | 10/2011 | Davidson et al. | |
| 2011/0244562 A1 | 10/2011 | Davidson et al. | |
| 2013/0281372 A1 | 10/2013 | McCray, Jr. et al. | |
| 2014/0163214 A1 | 6/2014 | Davidson et al. | |
| 2014/0179003 A1 | 6/2014 | Harper et al. | |
| 2014/0303362 A1 | 10/2014 | Davidson et al. | |

(Continued)

FOREIGN PATENT DOCUMENTS

| | | |
|---|---|---|
| WO | 9407529 | 4/1994 |
| WO | 2004047872 A2 | 6/2004 |

(Continued)

OTHER PUBLICATIONS

Anderson, et al., "Experimental validation of the importance of seed complement frequency to siRNA specificity", RNA 14, 853-861 (2008).

Bachevalier, et al., "Aged monkeys exhibit behavioral deficits indicative of widespread cerebral dysfunction", Neurobiol Aging 12, 99-111 (1991).

Birmingham, et al., "3' UTR seed matches, but not overall identity, are associated with RNAi off-targets", Nature Methods vol. 3 (3), 199-204 (2006).

(Continued)

*Primary Examiner* — Kate Poliakova-Georgantas

(74) *Attorney, Agent, or Firm* — Viksnins Harris & Padys PLLP

(57) ABSTRACT

The present invention is directed to RNA interference (RNAi) molecules targeted against a Huntington's disease nucleic acid sequence, and methods of using these RNAi molecules to treat Huntington's disease.

53 Claims, 6 Drawing Sheets

(56) References Cited

U.S. PATENT DOCUMENTS

2016/0060624 A1    3/2016    Davidson et al.

FOREIGN PATENT DOCUMENTS

| WO | 2005081714 A2 | 9/2005 |
|---|---|---|
| WO | 2005105995 A2 | 11/2005 |
| WO | 2006083800 A2 | 8/2006 |
| WO | 2007022506 | 2/2007 |
| WO | 2007051045 A2 | 5/2007 |
| WO | 2007089584 A2 | 8/2007 |
| WO | 2008134646 A2 | 11/2008 |
| WO | 2008134646 A3 | 11/2008 |
| WO | 2008150897 A2 | 12/2008 |
| WO | 2012109667 A1 | 8/2012 |

OTHER PUBLICATIONS

Birmingham, et al., "A protocol for designing siRNAs with high functionality and specificity", Nat Protoc 2 (9), 2068-2078 (2007).
Boden, "Enhanced gene silencing of HIV-1 specific siRNA using microRNA designed hairpins", Nucleic Acids Res, 32, 1154-1158, (2004).
Boudreau, et al., "Artificial MicroRNAs as siRNA Shuttles: Improved Safety as Compared to shRNAs in vitro and in vivo", Molecular Therapy vol. 17 (1), 169-175 (2009).
Boudreau, et al., "Minimizing variables among hairpin-based RNAi vectors reveals the potency of shRNAs", RNA 14, 1834-1844 (2008).
Boudreau, et al., "Nonallele-specific Silencing of Mutant and Wild-type Huntingtin Demonstrates Therapeutic Efficacy in Huntington's Disease Mice", Molecular Therapy vol. 17 (6), 1053-1063 (2009).
Boudreau, et al., "Rational design of therapeutic siRNAs: Minimizing off-targeting potential to improve the safety of RNAi therapy for Huntington's disease", Molecular Therapy vol. 19 (12), 2169-2177 (2011).
Bradford, et al., "Mutant huntingtin in glial cells exacerbates neurological symptoms of Huntington disease mice", J Biol Chem 285, 10653-10661 (2010).
Bramsen, et al., "A screen of chemical modifications identifies position-specific modification by UNA to most potently reduce siRNA off-target effects", Nucleic Acids Research vol. 38 (17), 5761-5773 (2010).
Brandenberger, GenBank direct submission Accession CN300012 (Feb. 4, 2011) [online]; downloaded from http://ncbi.nlm.nih.gov/nucest/CN300012 on May 31, 2012.
Burchard, et al., "MicroRNA-like off-target transcript regulation by siRNAs is species specific", RNA 15 (2), 308-315 (2009).
De Paula, "Hydrophobization and bioconjugation for enhanced siRNA delivery and targeting", RNA, 13, 431-456, (2007).
Denovan-Wright, "RNAi: a potential therapy for the dominantly inherited nucleotide repeat diseases", Gene Therapy, 13, 525-531, (2006).
Dodiya, et al., "Differential transduction following basal ganglia administration of distinct pseudotyped AAV capsid serotypes in nonhuman primates", Mol Ther 18, 579-587 (2010).
Fedorov, et al., "Off-target effects by siRNA can induce toxic phenotype", RNA 12, 1188-1196 (2006).
Franich, et al., "AAV vector-mediated RNAi of mutant huntingtin expression is neuroprotective in a novel genetic rat model of Huntington's disease", Mol Ther 16, 947-956 (2008).
Grimm, "Fatality in mice due to oversaturation of cellular microRNA/short hairpin RNA pathways", Nature, 441, 537-541,(2006).
Hadaczek, et al., "Transduction of nonhuman primate brain with adeno-associated virus serotype 1: vector trafficking and immune response", Hum Gene Ther 20, 225-237 (2009).
Halperin, et al., "Allegro: analyzing expression and sequence in concert to discover regulatory programs", Nucleic Acids Res 37 (5), 1566-1579 (2009).

Han, et al., "Molecular basis for the recognition of primary microRNAs by the Drosha-DGCR8 Complex", Cell, vol. 125, 887-901 (2006).
Harper, et al., "RNA interference improves motor and neuropathological abnormalities in a Huntington's disease mouse model", PNAS, vol. 102, 5820-5825 (2005).
Huang, et al., "High-capacity adenoviral vector-mediated reduction of huntingtin aggregate load in vitro and in vivo", Hum Gene Ther 18, 303-311 (2008).
Huang, et al., "The DAVID Gene Functional Classification Tool: a novel biological module-centric algorithm to functionally analyze large gene lists", Genome Biol 8 (9), R183 (2007).
Jackson, et al., "Position-specific chemical modification of siRNAs reduces "off-target" transcript silencing", RNA 12 (7), 1197-1205, (2006).
Johnson, et al., "Huntington's disease: progress toward effective disease-modifying treatments and a cure", Human Molecular Genetics, vol. 19 (1), R98-R102 (2010).
Khvorova, "Functional siRNAs and miRNAs Exhibit strand Bias", Cell, 115, 209-216 (1 supplementary page), (2003).
Landgraf, "A Mammalian microRNA Expression Atlas Based on Small RNA Library Sequencing", Cell, 129, 1401-1414, (2007).
Li, "Defining the optimal parameters for hairpin-based knockdown constructs", RNA, 13, 1765-1774, (2007).
Liu, et al., "Specific inhibition of Huntington's disease gene expression by siRNAs in cultured cells", Proc. Japan Acad., 79, Ser. B, No. 10, pp. 293-298, 2003.
McBride, et al., "Artificial miRNAs mitigate shRNA-mediated toxicity in the brain: Implications for the therapeutic levelopment of RNAi", PNAS, vol. 105, No. 15, pp. 5868-5873, 2008.
McBride, et al., "Preclinical Safety of RNAi-Mediated HTT Suppression in the Rhesus Macaque as a Potential Therapy for Huntington's Disease", Molecular Therapy vol. 19 (12), 2152-2162 (2011).
McMahon, "Optimisation of electrotransfer of plasmid into skeletal muscle by pretreatment with hyaluronidase—increased expression with reduced muscle damage", Gene Therapy 8, 1264-1270 (2001).
Miyagishi, "Optimization of an siRNA-expression system with an improved hairpin and its significant suppressive effects in mammalian cells", J. Gene Med., 6, 714-723, (2004).
Monteys, et al., "Single nucleotide seed modification restores in vivo tolerability of a toxic artificial miRNA sequence in the mouse brain", Nucleic Acids Res 42 (21), 13315-13327 (2014).
Patent Cooperation Treaty, International Searching Authority, Search Report and Written Opinion for PCT/US2015/031783, 12 pages, Sep. 17, 2015.
Penn, et al., "Probe #16038 for gene expression analysis in human heart cell sample", XP002733676, Database accession No. ABA37572, 2 pages (Jan. 23, 2002).
Pfister, et al., "Five siRNAs targeting three SNPs may provide therapy for three-quarters of Huntington's disease patients", Curr Biol 19, 774-778 (2009).
Rodriguez-Lebron, et al., "Intrastriatal rAAV-Mediated Delivery of Anti-huntingtin shRNAs Induces Partial Reversal of Disease Progression in R6/1 Huntington's Disease Transgenic Mice", Molecular Therapy vol. 12, No. 4, pp. 618-633, 2005.
Schwarz, "Asymmetry in the Assembly of the RNAi Enzyme Complex", Cell, 115, 199-208 (2003).
Silva, "Second-generation shRNA libraries covering the mouse and human genomes", Nature Genetics, 37, 1281-1288 (13 supplementary pages), (2005).
Smith, et al., "A simplified baculovirus-AV expression vector system coupled with one-step affinity purification yields high-titer rAAV stocks from insect cells", Mol Ther 17, 1888-1896 (2009).
Stegmeier, "A lentiviral microRNA-based system for single-compy polymerase II-regulated RNA interference in mammalian cells", PNAS, 102, 13212-13219 (3 supplementary pages), (2005).
Urabe, et al., "Insect cells as a factory to produce adeno-associated cirus type 2 vectors", Hum Gene Ther 13 (16), 1935-1943 (2002).
Vaish, et al., "Improved specificity of gene silencing by siRNAs containing unlocked nucleobase analogs", Nucleic Acids Research vol. 39 (5), 1823-1832 (2010).

(56) References Cited

OTHER PUBLICATIONS

Vermeulen, "The contributions of dsRNA structure to Dicer specificity and efficiency", RNA, 11, 674-682, (2005).

Wang, et al., "Clinico-pathological rescue of a model mouse of Huntington's disease by siRNA", Neuroscience Research 53, pp. 241-249, 2005.

Xia, "RNAi suppresses polyglutamine-induced neurodegeneration in a model of spinocerebellar ataxia", Nature Medicine, 10, 816-820 (4 supplementary pages), (2004).

Zeng, et al., "Structural requirements for pre-microRNA binding and nuclear export by Exportin 5", Nucleic Acids Research vol. 32 (16), 4776-4785 (2004).

Figure 2
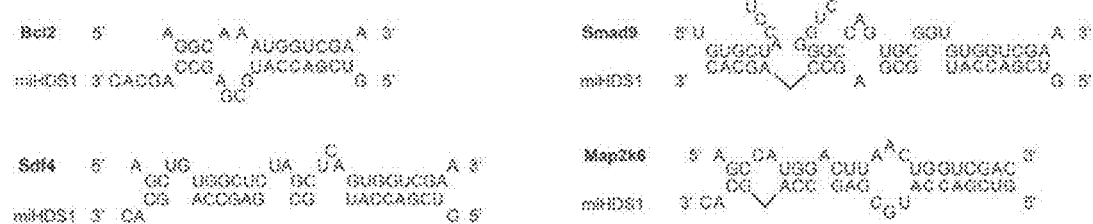
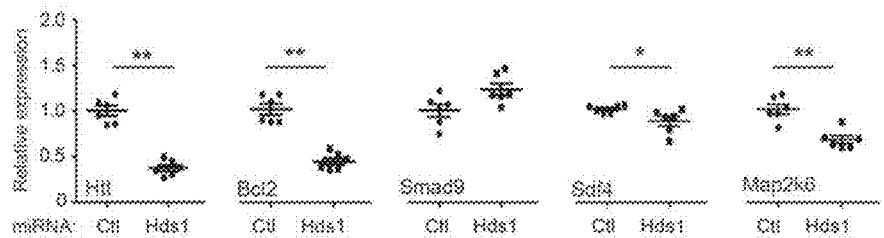
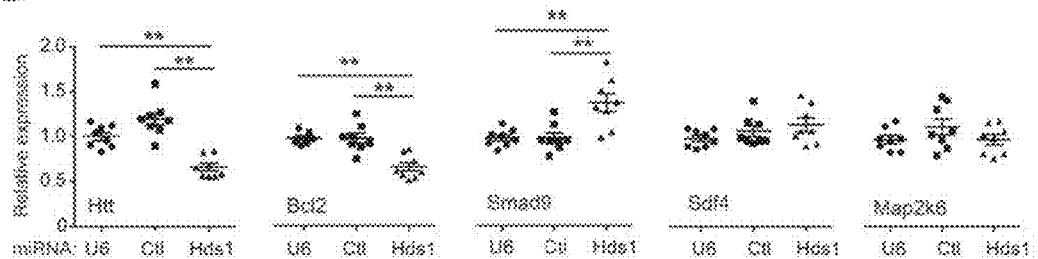

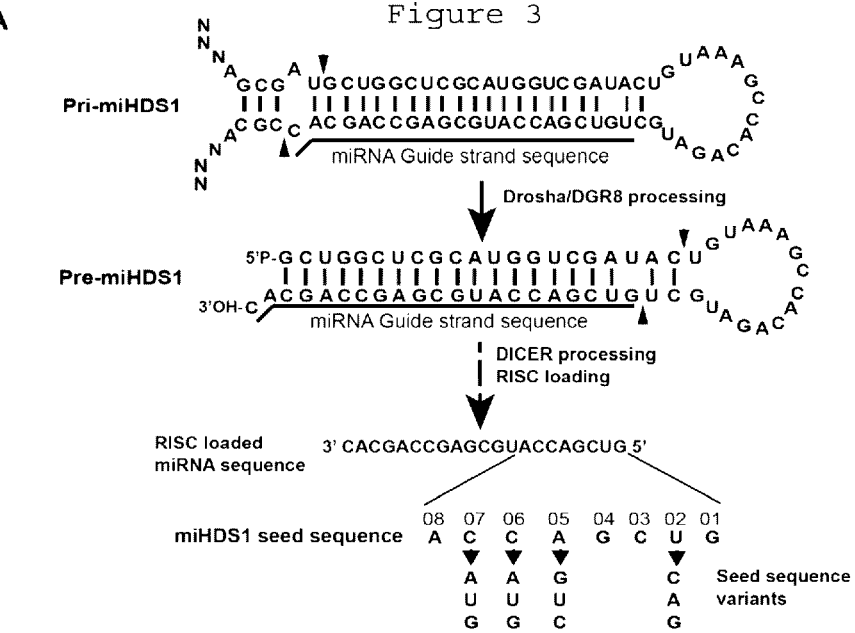

HDS1 variants SPS on HDS1 targets (ΔG: -13.13 Kcal/mol)

| Variants 2 | Variants 5 | Variants 6 | Variants 7 |
| --- | --- | --- | --- |
| HDS1v2C: -11.55 Kcal/mol | HDS1v5G: -6.53 Kcal/mol | HDS1v6A: -8.1 Kcal/mol | HDS1v7A: -9.45 Kcal/mol |
| HDS1v2A: -11.55 Kcal/mol | HDS1v5U: -6.53 Kcal/mol | HDS1v6U: -8.1 Kcal/mol | HDS1v7U: -9.45 Kcal/mol |
| HDS1v2G: -11.55 Kcal/mol | HDS1v5C: -6.53 Kcal/mol | HDS1v6G: -8.1 Kcal/mol | HDS1v7G: -9.45 Kcal/mol |

C

| | Overall Target Genes | | Striatum-Expressed Genes | |
| --- | --- | --- | --- | --- |
| miRNA | #Target Genes | #Shared with HDS1 | #Target Genes | #Shared with HDS1 |
| HDS1 | 197 | 197 | 170 | 170 |
| 2U>A | 288 | 5 | 254 | 5 |
| 2U>C | 350 | 9 | 318 | 8 |
| 2U>G | 270 | 7 | 234 | 7 |
| 3C>A | 1611 | 41 | 1381 | 37 |
| 3C>G | 1704 | 31 | 1433 | 26 |
| 3C>U | 1501 | 34 | 1246 | 33 |
| 4G>A | 1803 | 38 | 1561 | 35 |
| 4G>C | 2409 | 58 | 2088 | 53 |
| 4G>U | 1998 | 41 | 1719 | 37 |
| 5A>C | 329 | 10 | 279 | 8 |
| 5A>G | 408 | 10 | 366 | 9 |
| 5A>U | 361 | 13 | 317 | 13 |
| 6C>A | 298 | 7 | 266 | 7 |
| 6C>G | 346 | 8 | 310 | 8 |
| 6C>U | 241 | 4 | 205 | 3 |
| 7C>A | 329 | 12 | 287 | 11 |
| 7C>G | 54 | 2 | 46 | 2 |
| 7C>U | 228 | 6 | 188 | 6 |

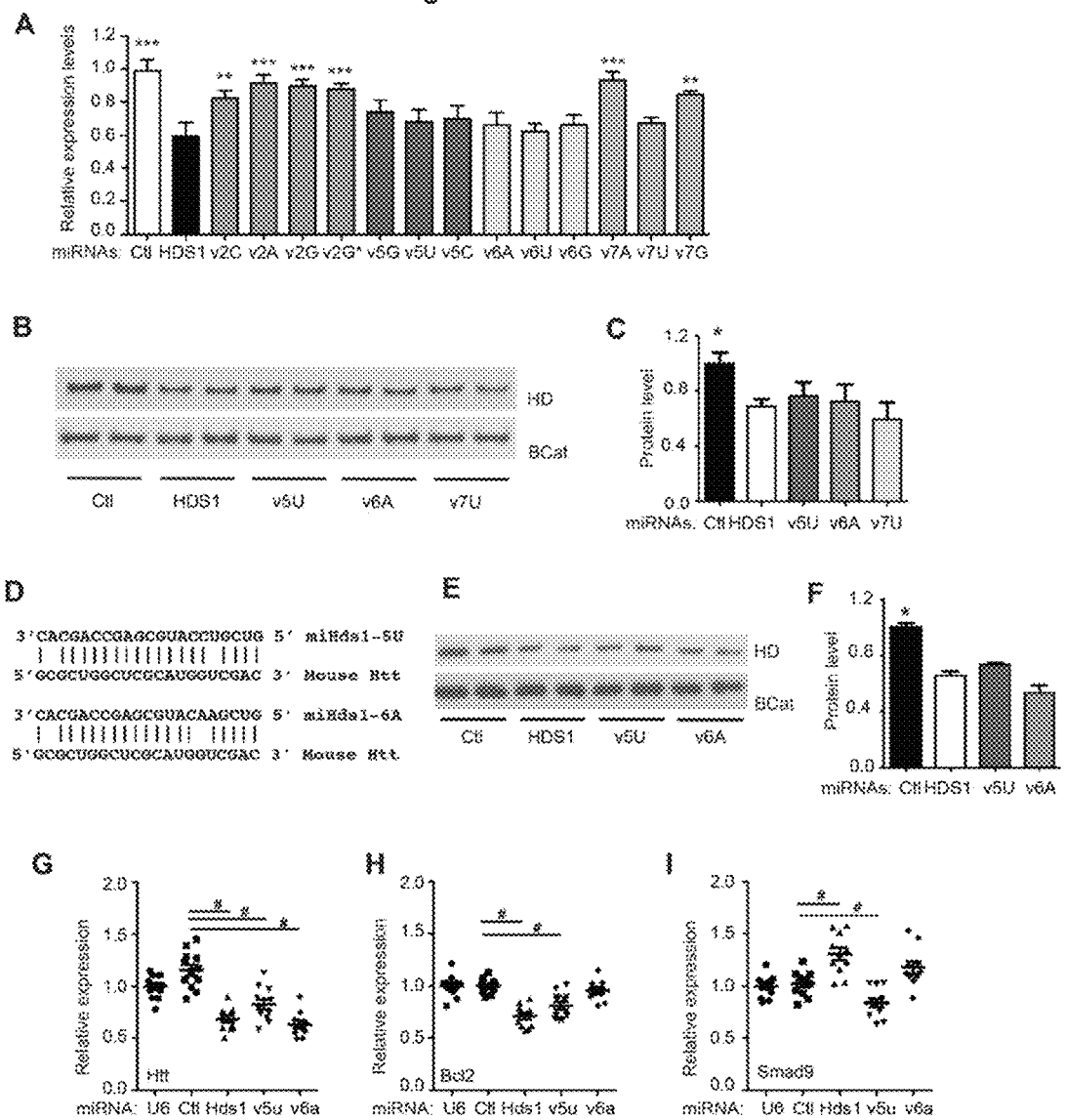

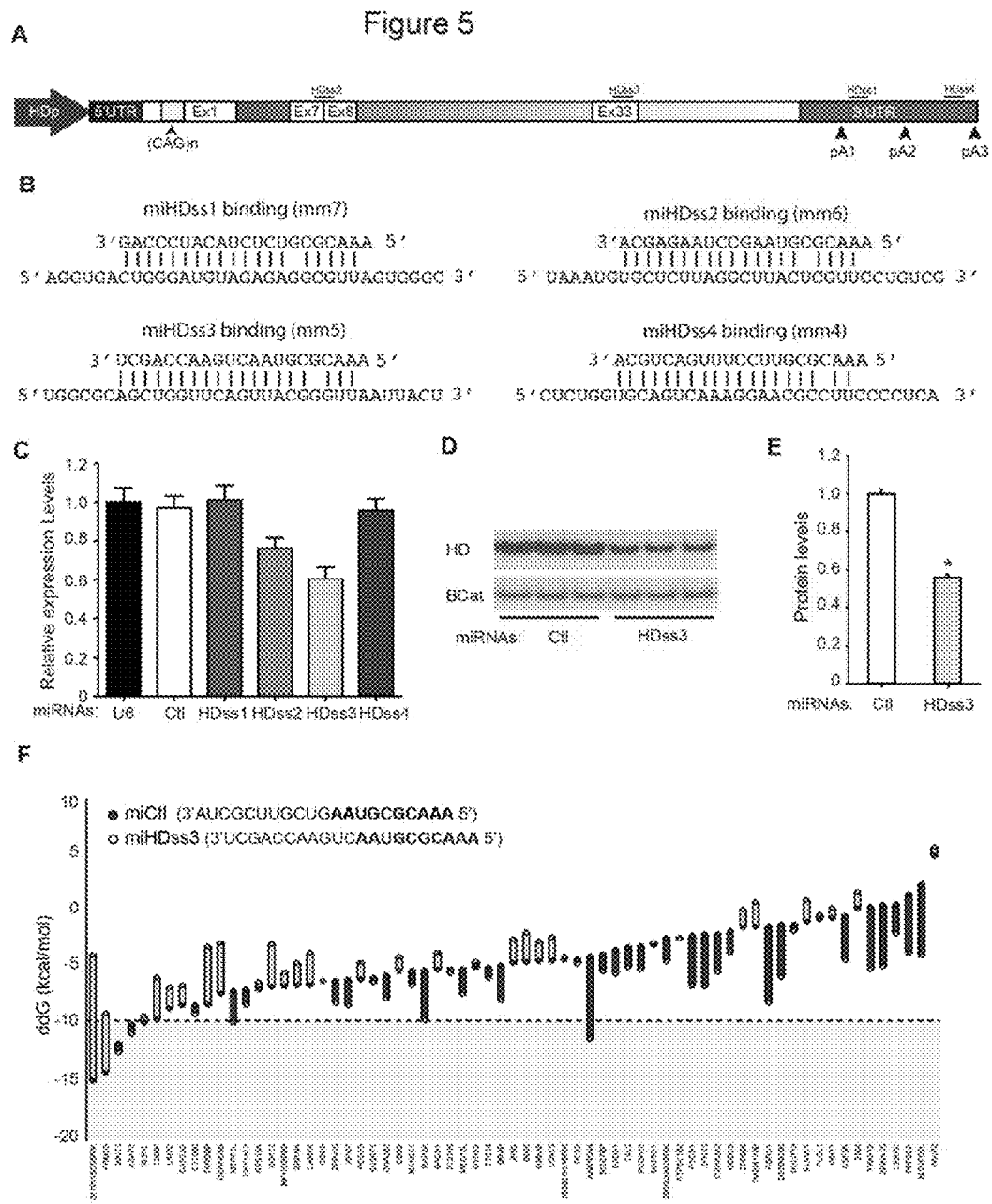

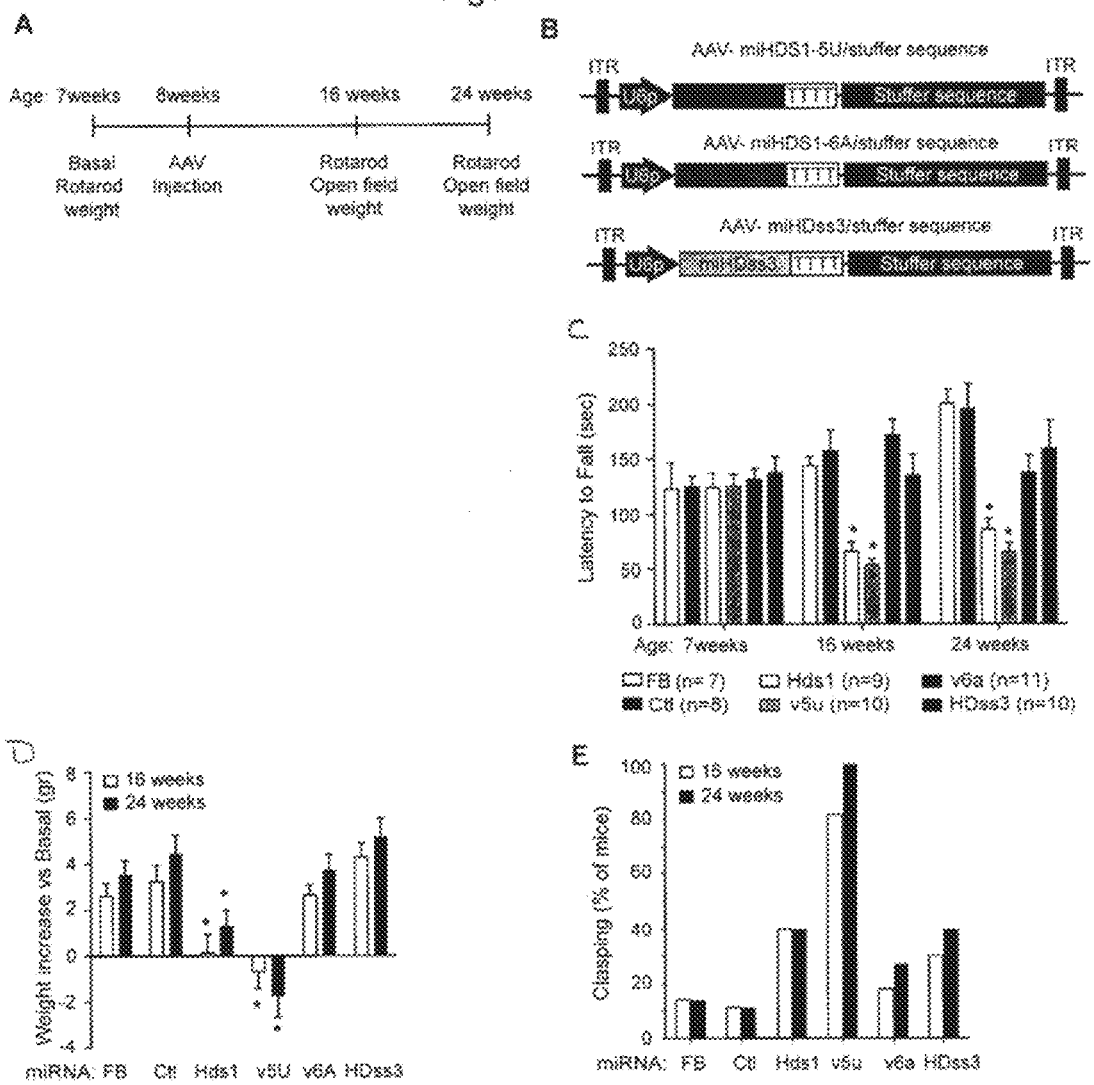

SEQUENCE LISTING

<160> NUMBER OF SEQ ID NOS: 85

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
gucgaccaug cgagccagca c                                              21

<210> SEQ ID NO 2
<211> LENGTH: 21
<212> TYPE: RNA
<213> ORGANISM: Mus musculus

<400> SEQUENCE: 2
gcgcuggcuc gcauggucga c                                              21

<210> SEQ ID NO 3
<211> LENGTH: 21
<212> TYPE: RNA
<213> ORGANISM: Homo sapiens

<400> SEQUENCE: 3

```
gugcuggcuc gcauggucga c                                              21
```

<210> SEQ ID NO 4
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, c, u, g, unknown or other
<220> FEATURE:
<221> NAME/KEY: modified_base
<222> LOCATION: (74)..(76)
<223> OTHER INFORMATION: a, c, u, g, unknown or other

<400> SEQUENCE: 4

```
nnnagcgaug cuggcucgca uggucgauac uguaaagcca cagaugcugu cgaccaugcg    60
agccagcacc gcannn                                                    76
```

<210> SEQ ID NO 5
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5

```
gcuggcucgc auggucgaua cuguaaagcc acagaugcug ucgaccaugc gagccagcac    60
```

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6

```
gucguccaug cgagccagca c                                              21
```

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7

```
gucgaacaug cgagccagca c                                              21
```

<210> SEQ ID NO 8
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, c, u, g, unknown or other
<220> FEATURE:
<221> NAME/KEY: modified_base
<222> LOCATION: (74)..(76)

<223> OTHER INFORMATION: a, c, u, g, unknown or other

<400> SEQUENCE: 8
nnnagcgaug cuggcucgca uggucgauac uguaaagcca cagaugcugu cguccaugcg    60
agccagcacc gcannn    76

<210> SEQ ID NO 9
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, c, u, g, unknown or other
<220> FEATURE:
<221> NAME/KEY: modified_base
<222> LOCATION: (74)..(76)
<223> OTHER INFORMATION: a, c, u, g, unknown or other

<400> SEQUENCE: 9
nnnagcgaug cuggcucgca uggucgauac uguaaagcca cagaugcugu cgaacaugcg    60
agccagcacc gcannn    76

<210> SEQ ID NO 10
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
gcuggcucgc auggucgaua cuguaaagcc acagaugcug ucguccaugc gagccagcac    60

<210> SEQ ID NO 11
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
gcuggcucgc auggucgaua cuguaaagcc acagaugcug ucgaacaugc gagccagcac    60

<210> SEQ ID NO 12
<211> LENGTH: 163
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 12
gcguuuagug aaccgucaga ugguaccguu uaaacucgag ugagcgaugc uggcucgcau    60
ggucgauacu guaaagccac agaugggugu cgaccaugcg agccagcacc gccuacuaga   120
gcggccgcca cagcggggag auccagacau gauaagauac auu   163

<210> SEQ ID NO 13
<211> LENGTH: 8
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 13 gugagcga                                                                  8

<210> SEQ ID NO 14
<211> LENGTH: 8
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14 gugagcgc                                                                  8

<210> SEQ ID NO 15
<211> LENGTH: 9
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15 uaaacucga                                                                 9

<210> SEQ ID NO 16
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
ugguaccguu                                                               10

<210> SEQ ID NO 17
<211> LENGTH: 7
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17 cgcyuac                                                                   7

<210> SEQ ID NO 18
<211> LENGTH: 7
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18 cgccuac                                                                   7

<210> SEQ ID NO 19
<211> LENGTH: 11
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 19
agcggccgcc a                                                            11

<210> SEQ ID NO 20
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(17)
<223> OTHER INFORMATION: a, c, u, g, unknown or other

<400> SEQUENCE: 20
cunnnnnnnn nnnnnnngg                                                    19

<210> SEQ ID NO 21
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(17)
<223> OTHER INFORMATION: a, c, u, g, unknown or other

<400> SEQUENCE: 21
ccnnnnnnnn nnnnnnngg                                                    19

<210> SEQ ID NO 22
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
cugugaagcc acagauggg                                                    19

<210> SEQ ID NO 23
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
ccgugaagcc acagauggg                                                    19

<210> SEQ ID NO 24
<211> LENGTH: 2
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24 uu                                                                       2
```

```
<210> SEQ ID NO 25
<211> LENGTH: 3
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25 uuu                                                                        3

<210> SEQ ID NO 26
<211> LENGTH: 4
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26 uuuu                                                                       4

<210> SEQ ID NO 27
<211> LENGTH: 3
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27 cuu                                                                        3

<210> SEQ ID NO 28
<211> LENGTH: 4
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28 cuuu                                                                       4

<210> SEQ ID NO 29
<211> LENGTH: 5
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29 cuuuu                                                                      5

<210> SEQ ID NO 30
<211> LENGTH: 3
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30 uag                                                                        3
```

```
<210> SEQ ID NO 31
<211> LENGTH: 15
<212> TYPE: RNA
<213> ORGANISM: Mus musculus

<400> SEQUENCE: 31
aggcaaaugg ucgaa                                                          15

<210> SEQ ID NO 32
<211> LENGTH: 42
<212> TYPE: RNA
<213> ORGANISM: Mus musculus

<400> SEQUENCE: 32
ugugcuaccu acuuaaccug gggccagugc ggguguggucg aa                           42

<210> SEQ ID NO 33
<211> LENGTH: 27
<212> TYPE: RNA
<213> ORGANISM: Mus musculus

<400> SEQUENCE: 33
agcuguggcu cuagcucagu ggucgaa                                             27

<210> SEQ ID NO 34
<211> LENGTH: 23
<212> TYPE: RNA
<213> ORGANISM: Mus musculus

<400> SEQUENCE: 34
agccauggac uuaacgguc gac                                                  23

<210> SEQ ID NO 35
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
aaacgcgucu cuacauccca g                                                   21

<210> SEQ ID NO 36
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
aaacgcguaa gccuaagagc a                                                   21

<210> SEQ ID NO 37
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
aaacgcguaa cugaaccagc u                                                   21
```

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
aaacgcguuc cuuugacugc a                                              21

<210> SEQ ID NO 39
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
aaacgcguaa gucguucgcu a                                              21

<210> SEQ ID NO 40
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
aggugacugg gauguagaga ggcguuagug ggc                                 33

<210> SEQ ID NO 41
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
uaaaugugcu cuuaggcuua cucguuccug ucg                                 33

<210> SEQ ID NO 42
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
uggcgcagcu gguucaguua cggguuaauu acu                                 33

<210> SEQ ID NO 43
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
cucuggugca gucaaaggaa cgccuucccc uca                                 33

```
<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid

<400> SEQUENCE: 44

Pro Xaa Xaa Pro Ser
1               5

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Any amino acid

<400> SEQUENCE: 45

Ser Pro Xaa Xaa Pro
1               5

<210> SEQ ID NO 46
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Thr Leu His
1

<210> SEQ ID NO 47
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 47

Gln Ser Xaa Tyr
1

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Pro Tyr Phe Pro Ser Leu Ser
```

```
<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Tyr Ala Pro Leu Thr Pro Ser
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Pro Leu Ser Pro Ser Ala Tyr
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asp Ser Pro Ala His Pro Ser
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Thr Pro Thr His Pro Ser
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Pro Asp Ala Pro Ser Asn His
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 54

Thr Glu Pro His Trp Pro Ser
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Pro Pro Leu Pro Pro Lys
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ser Pro Lys Pro Pro Pro Gly
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Asn Trp Ser Pro Trp Asp Pro
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asp Ser Pro Ala His Pro Ser
1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Trp Thr Leu His Asn Lys
1               5

<210> SEQ ID NO 60

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Lys Ile Pro Pro Thr Leu His
1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ile Ser Gln Thr Leu His Gly
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Ser Phe Tyr Ile Leu Thr
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Thr Thr Gln Ser Glu Tyr Gly
1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Met Asn Ala Phe Arg Ala
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65
```

```
Gly Tyr Glu Ser Gln Thr Thr
1               5

<210> SEQ ID NO 66
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid

<400> SEQUENCE: 66

Leu Xaa Ser Ser
1

<210> SEQ ID NO 67
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 67

Pro Phe Xaa Gly
1

<210> SEQ ID NO 68
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 68

Ser Ile Xaa Ala
1

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Met Leu Val Ser Ser Pro Ala
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 70

Leu Pro Ser Ser Leu Gln Lys
1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Pro Pro Leu Leu Lys Ser Ser
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid

<400> SEQUENCE: 72

Pro Xaa Lys Leu Asp Ser Ser
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ala Trp Thr Leu Ala Ser Ser
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Trp Pro Phe Tyr Gly Thr Pro
1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Thr Phe Pro Phe Leu Gly
1               5
```

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Gln Val Pro Phe Met Gly
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ala Asn Phe Ser Ile Leu Ala
1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Ser Ile Trp Ala Pro Ala
1               5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ser Ile Ala Ala Ser Phe Ser
1               5

<210> SEQ ID NO 80
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Thr His Arg Pro Pro Met Trp Ser Pro Val Trp Pro
1               5                   10

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 81

Cys Arg Thr Ile Gly Pro Ser Val Cys
1               5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gly His Lys Val Lys Arg Pro Lys Gly
1               5

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Lys Asp Lys Ile Lys Met Asp Lys Lys
1               5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly His Lys Ala Lys Gly Pro Arg Lys
1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Lys Trp Lys Thr Pro Lys Val Arg Val
1               5
```

HUNTINGTON'S DISEASE THERAPEUTIC COMPOUNDS

RELATED APPLICATION

This application claims priority to U.S. Provisional Patent Application No. 62/000,895, filed May 20, 2014, the entirety of which is incorporated herein by reference.

GOVERNMENT SUPPORT

The invention was made with Government support under, DK054759, NS050210 and NS068099 awarded by The National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, is named 17023.149WO1_SL.txt.

BACKGROUND OF THE INVENTION

RNAi directs sequence-specific gene silencing by double-stranded RNA (dsRNA) which is processed into functional small inhibitory RNAs (~21 nt). In nature, RNAi for regulation of gene expression occurs primarily via small RNAs known as microRNAs (miRNAs). Mature microRNAs (~19-25 nucleotides) are processed from larger primary miRNA transcripts (pri-miRNAs) which contain stem-loop regions. Via a series of processing events catalyzed by the ribonucleases, Drosha and Dicer, the miRNA duplex region is liberated and a single strand (the antisense "guide" strand) is then incorporated into the RNA Induced Silencing Complex (RISC), thus generating a functional complex capable of base-pairing with and silencing target transcripts. The mode of target repression primarily depends upon the degree of complementarity; transcript cleavage typically requires a high-degree of base-pairing, whereas translational repression and mRNA destabilization occurs when small RNAs bind imperfectly to target transcripts (most often in the 3' UTR). Indeed for the latter, short stretches of complementarity—as little as 6 bp—may be sufficient to cause gene silencing.

SUMMARY OF THE INVENTION

The present invention provides an isolated miRNA shuttle vector that expresses a therapeutic siRNA with limited off target toxicity. In certain embodiments, embedding an siRNA that exhibits off target toxicity in the context of an miRNA shuttle vector of the present invention limits the off target toxicity of the siRNA. In certain embodiments, the miRNA shuttle vector expresses a therapeutic siRNA in the brain with limited off target toxicity. In certain embodiments, the miRNA shuttle vector expresses a therapeutic siRNA in the striatum with limited off target toxicity. In certain embodiments, the miRNA shuttle vector expresses a therapeutic siRNA in the cerebrum with limited off target toxicity.

The present invention provides an isolated nucleic acid encoding a primary transcript (pri-miRNA) including, in order of position, a 5'-flanking region, a non-guide (passenger) region, a loop region, a guide region, and a 3'-flanking region, wherein the guide region consists of SEQ ID NO: 37 (miHDss3), SEQ ID NO:6 (miHDS1v5U) or SEQ ID NO:7 (miHDS1v6A), and the non-guide region is at least 80% complementary to the guide region. In certain embodiments, the non-guide region is at least 81%, 82%, 83%, 84%, 85%, 86%, 87%, 88%, 89%, 90%, 91%, 92%, 93%, 94%, 95%, 96%, 97%, 98%, 99% or 100% complementary to the guide region. In certain embodiments, the 5'-flanking region is contiguously linked to the non-guide region, the loop region is positioned between the non-guide region and the guide region, and the guide region is contiguously linked to the 3'-flanking region. As used herein, the term "siRNA guide region" is a single-stranded sequence of RNA that is complementary to a target sequence. As used herein, the term "siRNA non-guide region" is a single-stranded sequence of RNA that is complementary to the "siRNA guide region." Thus, under the proper conditions, the siRNA guide region and the siRNA non-guide region associate to form an RNA duplex. As used herein, all nucleic acid sequences are listed, as is customary, in a 5' to 3' direction.

In certain embodiments, the 5'-flanking region contains a 5'-joining sequence contiguously linked to the non-guide region. As used herein, the term "joining site" or a "joining sequence" is a short nucleic acid sequence of less than 60 nucleotides that connects two other nucleic acid sequences. In certain embodiments, the joining site is of a length of any integer between 4 and 50, inclusive. In certain embodiments, the 5'-joining sequence consists of 5-8 nucleotides (e.g., consists of 6 nucleotides). In certain embodiments, the 5'-joining sequence encodes GUGAGCGA (SEQ ID NO:13) or GUGAGCGC (SEQ ID NO:14).

In certain embodiments, the 5'-flanking region further comprises a 5'-bulge sequence positioned upstream from the 5'-joining sequence. As used herein, the term "bulge sequence" is a region of nucleic acid that is non-complementary to the nucleic acid opposite it in a duplex. For example, a duplex will contain a region of complementary nucleic acids, then a region of non-complementary nucleic acids, followed by a second region of complementary nucleic acids. The regions of complementary nucleic acids will bind to each other, whereas the central non-complementary region will not bind, thereby forming a "bulge." In certain embodiments the two strands of nucleic acid positioned between the two complementary regions will be of different lengths, thereby forming a "bulge." In certain embodiments, the 5'-bulge sequence will contain from 2 to 15 nucleotides. In certain embodiments, the 5'-bulge sequence consists of about 1-10 nucleotides. In certain embodiments, the 5'-bulge sequence encodes UAAACUCGA (SEQ ID NO: 15). In certain embodiments, the 5'-bulge sequence has from 0-50% complementarity to the 3'-bulge sequence.

In certain embodiments, the 5'-flanking region further contains a 5'-spacer sequence positioned upstream from the 5'-bulge sequence. In certain embodiments, the 5'-spacer sequence consists of 9-12 nucleotides, such as 10-12 nucleotides. In certain embodiments, the 5'-spacer sequence has from 60-100% complementarity to a 3'-spacer sequence. In certain embodiments, the 5'-bulge sequence comprises a cloning site, such as an XhoI site. In certain embodiments, the 5'-spacer sequence is UGGUACCGUU (SEQ ID NO: 16).

In certain embodiments, the 5'-flanking region further contains a 5'-upstream sequence positioned upstream from the 5'-spacer sequence. In certain embodiments, the 5'-upstream sequence is about 5-5000 nucleotides in length, such as 30-2000 nucleotides in length.

In certain embodiments, the 3'-flanking region contains a 3'-joining sequence contiguously linked to the guide region. In certain embodiments, the joining site is of a length of any integer between 4 and 50, inclusive. In certain embodiments, the 3'-joining sequence consists of 5-8 nucleotides, (e.g., consists of 6 nucleotides). In certain embodiments, the 3'-joining sequence is at least about 85% complementary to a 5'-joining sequence. In certain embodiments, the 3'-joining sequence encodes CGCYUAC (SEQ ID NO: 17), wherein Y is C or U. In certain embodiments, the 3'-joining sequence encodes CGCCUAC (SEQ ID NO: 18).

In certain embodiments, the 3'-flanking region further comprises a 3'-bulge sequence positioned downstream from the 3'-joining sequence. In certain embodiments, the 3'-bulge sequence comprises a cloning site, such as a SpeI/XbaI site or a SpeI site. In certain embodiments, the 3'-bulge sequence consists of about 1-15 nucleotides (such as 2-15 nucleotides or 1-10 nucleotides). In certain embodiments, the 3'-bulge sequence encodes UAG (SEQ ID NO: 30). In certain embodiments, the 5'-bulge sequence is complementary to the 3'-bulge sequence at only one nucleotide at each end of the sequence.

In certain embodiments, the 3'-flanking region further contains a 3'-spacer sequence positioned downstream from the 3'-bulge sequence. In certain embodiments, the 3'-spacer sequence consists of 9-12 nucleotides, such as 10-12 nucleotides. In certain embodiments, the 3'-spacer sequence is AGCGGCCGCCA (SEQ ID NO: 19). In certain embodiments, the 3'-spacer sequence is at least about 0.70% complementary to a 5'-spacer sequence.

In certain embodiments, the 3'-flanking region further contains a 3'-downstream sequence positioned downstream from the 3'-spacer sequence. In certain embodiments, a 5'-upstream sequence does not significantly pair with the 3'-downstream sequence. As used herein, the term "does not significantly pair with" means that the two strands are less than 20% homologous. In certain embodiments, the 3'-downstream sequence is about 5-5000 nucleotides in length, such as 30-2000 nucleotides in length.

In certain embodiments, the loop region is from 4-20 nucleotides in length, such as 15-19 nucleotides in length. From 0-50% of the loop region can be complementary to another portion of the loop region. As used herein, the term "loop region" is a sequence that joins two complementary strands of nucleic acid. In certain embodiments, 1-3 nucleotides of the loop region are immediately contiguous to the complementary strands of nucleic acid may be complementary to the last 1-3 nucleotides of the loop region. For example, the first two nucleic acids in the loop region may be complementary to the last two nucleotides of the loop region. In certain embodiments, the loop region is 17 nucleotides in length. In certain embodiments, the loop region encodes CUNNNNNNNNNNNNNNNGG (SEQ ID NO:20) or CCNNNNNNNNNNNNNNNGG (SEQ ID NO:21). In certain embodiments, the loop region encodes CUGUGAAGCCACAGAUGGG (SEQ ID NO:22) or CCGUGAAGCCACAGAUGGG (SEQ ID NO:23).

The present invention further provides an RNA encoded by nucleic acid described herein.

The present invention further provides an expression cassette containing a promoter contiguously linked to a nucleic acid described herein. In certain embodiments, the promoter is a polII or a polIII promoter, such as a U6 promoter (e.g., a mouse U6 promoter). In certain embodiments, the expression cassette further contains a marker gene. In certain embodiments, the promoter is a polII promoter. In certain embodiments, the promoter is a tissue-specific promoter. In certain embodiments, the promoter is an inducible promoter. In certain embodiments, the promoter is a polIII promoter.

In certain embodiments, the expression cassette further comprises a marker gene.

The present invention provides a vector containing an expression cassette described herein. In certain embodiments, the vector is an adeno-associated virus (AAV) vector. In certain embodiments, the AAV is AAV1, AAV2, AAV5, AAV6 and/or AAV9. In certain embodiments, the AAV is AAV2. In certain embodiments, the AAV is AAV2/1. Examples of such AAVs are found in Davidson et al., PNAS (2000) 97:3428-3432. In certain embodiments, the AAV is AAV2/1. In certain embodiments, the AAV is AAV2/5. As used herein, the term AAV2/1 is used to mean an AAV2 ITR and AAV1 capsid, the term AAV2/2 is an AAV2 ITR and AAV2 capsid, the term AAV2/4 is an AAV2 ITR and AAV4 capsid, etc. In certain embodiments, the AAV is AAV1, AAV2, AAV5, AAV6 and/or AAV9. In certain embodiments, the AAV is AAV1. In certain embodiments, the AAV is AAV2. In certain embodiments, the AAV is AAV5. In certain embodiments, the AAV is an AAV6. In certain embodiments, the AAV is an AAV8. In certain embodiments, the AAV is an AAV9. In certain embodiments, the AAV is an AAVrh10.

In certain embodiments, the AAV capsid has at least 80% homology to any reference AAV serotype capsid protein VP1, VP2, and/or VP3, e.g., to a AAV1 capsid protein VP1, VP2, and/or VP3, or e.g., to a AAV2 capsid protein VP1, VP2, and/or VP3, or e.g., a AAV3 capsid protein VP1, VP2, and/or VP3, or e.g., a AAV4 capsid protein VP1, VP2, and/or VP3, or e.g., a AAV5 capsid protein VP1, VP2, and/or VP3, or e.g., a AAV6 capsid protein VP1, VP2, and/or VP3, or e.g., a AAV7 capsid protein VP1, VP2, and/or VP3, or e.g., a AAV8 capsid protein VP1, VP2, and/or VP3, or e.g., a AAV9 capsid protein VP1, VP2, and/or VP3, or e.g., a AAVrh10 capsid protein VP1, VP2, and/or VP3, or e.g., a AAVrh74 capsid protein VP1, VP2, and/or VP3.

In certain embodiments, the AAV capsid has 100% homology to any reference AAV serotype capsid protein VP1, VP2, and/or VP3, e.g., to a AAV1 capsid protein VP1, VP2, and/or VP3, or e.g., to a AAV2 capsid protein VP1, VP2, and/or VP3, or e.g., a AAV3 capsid protein VP1, VP2, and/or VP3, or e.g., a AAV4 capsid protein VP1, VP2, and/or VP3, or e.g., a AAV5 capsid protein VP1, VP2, and/or VP3, or e.g., a AAV6 capsid protein VP1, VP2, and/or VP3, or e.g., a AAV7 capsid protein VP1, VP2, and/or VP3, or e.g., a AAV8 capsid protein VP1, VP2, and/or VP3, or e.g., a AAV9 capsid protein VP1, VP2, and/or VP3, or e.g., a AAVrh10 capsid protein VP1, VP2, and/or VP3, or e.g., a AAVrh74 capsid protein VP1, VP2, and/or VP3.

The present invention provides a non-human animal comprising the nucleic acid, the expression cassette, the vector or duplex described herein.

The present invention provides an isolated nucleic acid between 80-4000 nucleotides in length comprising a nucleic acid encoding an artificial primary miRNA transcript (pri-miRNA) consisting of, in order of position, a 5'-flanking region, a non-guide region, a loop region, a guide region, and a 3'-flanking region, wherein the guide region consists of SEQ ID NO: 37 (miHDss3), SEQ ID NO:6 (miHDS1v5U) or SEQ ID NO:7 (miHDS1v6A), and the non-guide region is at least 80% complementary to the guide region.

The present invention provides an isolated nucleic acid consisting of Pri-miHDS1 v5U (SEQ ID NO:8), Pri-miHDS1v6A (SEQ ID NO:9), Pre-miHDS1v5U (SEQ ID NO:10), or Pre-miHDS1v6A (SEQ ID NO: 11). In one embodiment, a full-length miHDS1 (SEQ ID NO:12) has the following sequence:

(SEQ ID NO: 12)
5'-
GCGUUUAGUGAACCGUCAGAUGGUACCGUUUAAACUCGAGUGAGCGAUGC

UGGCUCGCAUGGUCGAUACUGUAAAGCCACAGAUGGGUGUCGACCAUGCG

AGCCAGCACCGCCUACUAGAGCGGCCGCCACAGCGGGGAGAUCCAGACAU

GAUAAGAUACAUU-3'

The present invention provides an isolated RNA duplex comprising a guide region of nucleic acid and a non-guide region of nucleic acid, wherein the guide region is SEQ ID NO: 37 (miHDss3), SEQ ID NO:6 (miHDS1v5U) or SEQ ID NO:7 (miHDS1v6A) and the non-guide region is at least 80% complementary to the guide region. In certain embodiments, the isolated RNA duplex is between 19-30 base pairs in length. Certain embodiments include an expression cassette encoding the isolated nucleic acid described above. In certain embodiments the expression cassette further comprises a marker gene.

The present invention provides method of inducing RNA interference by administering to a subject a nucleic acid, an expression cassette, a vector, or a composition described herein.

The present invention provides a vector containing a U6 promoter operably linked to a nucleic acid encoding an miRNA. The predicted transcription start sites of constructs of the present invention are different from those used by researchers in the past. In certain embodiments of the present invention, the U6miRNA has an extended 5' end. If the 5' end is truncated to resemble the previous CMV-based strategy, silencing efficacy is severely reduced. The present invention also provides improved flanking sequences that show improved efficacy over natural miR-30 flanking sequences. The use of the present miRNA strategy appears to alleviate toxicity associated with traditional shRNA approaches. The miRNA strategy does not generally generate excessive amounts of RNAi as do U6shRNA approaches.

As used herein the term "stem sequence" is a sequence that is complementary to another sequence in the same molecule, where the two complementary strands anneal to form a duplex (e.g., the non-guide and guide regions). The duplex that is formed maybe fully complementary, or may be less than fully complementary, such as 99%, 98%, 97%, 96%, 95,%, 94%, 93%, 92%, 91%, 90%, 89%, 88%, 87%, 86%, 85%, 84%, 83%, 82%, 81%, 80%, 75%, or 70% complementary to each other. Further, in certain embodiments, one strand may contain more nucleotides than the other strand, allowing the formation of a side loop.

The present invention also provides vectors containing the expression cassettes described herein. Examples of appropriate vectors include adenoviral, lentiviral, adeno-associated viral (AAV), poliovirus, herpes simplex virus (HSV), or murine Maloney-based viral vectors. In one embodiment, the vector is an adeno-associated virus vector. These cassettes and vectors may be contained in a cell, such as a mammalian cell. A non-human mammal may contain the cassette or vector.

The present invention provides cells (such as a mammalian cell) containing the nucleic acid molecules, expression cassettes or vectors described herein. The present invention also provides a non-human mammal containing the nucleic acid molecules, expression cassettes or vectors described herein.

The present invention provides a nucleic acid, an expression cassette, a vector, or a composition as described herein for use in therapy, such as for treating a neurodegenerative disease.

The present invention provides an isolated RNAi molecule having a microRNA having an overhang at the 3' end. In certain embodiments, the overhang is a 2 to 5-nucleotide repeat. In certain embodiments, the overhang is a UU (SEQ ID NO:24), UUU (SEQ ID NO:25), UUUU (SEQ ID NO:26), CUU (SEQ ID NO:27), CUUU (SEQ ID NO:28) or CUUUU (SEQ ID NO:29) sequence. In certain embodiments, the microRNA is a naturally-occurring microRNA. In certain embodiments, microRNA is an artificial microRNA. In certain embodiments, the RNAi molecule produces a decreased level of off-target toxicity.

The present invention provides a method of inducing low-toxicity RNA interference by administering to a subject a nucleic acid, an expression cassette, a vector, or a composition as described herein. In certain embodiments, the expression cassette contains a polII promoter.

The present invention provides a method of inducing low-toxicity RNA interference by administering to a subject an expression cassette encoding a polIII promoter operably linked to a nucleic acid encoding a miRNA. In certain embodiments, the miRNA comprises a 2- or 3-nucleotide 5' or 3'-overhang. In certain embodiments, the miRNA comprises a 2-nucleotide 3'-overhang. In certain embodiments, the miRNA is an artificial miRNA.

The present invention provides a method of treating a subject with a Huntington's Disease by administering to the subject a nucleic acid, an expression cassette, a vector, or a composition as described herein so as to treat the Huntington's Disease.

The present invention provides a method of suppressing the accumulation of huntingtin in a cell by introducing nucleic acid molecules (e.g., a ribonucleic acid (RNA)) described herein into the cell in an amount sufficient to suppress accumulation of huntingtin in the cell. In certain embodiments, the accumulation of huntingtin is suppressed by at least 10%. In certain embodiments, the accumulation of huntingtin is suppressed by at least 10%, 20%, 30%, 40%, 50%, 60%, 70%, 80%, 90% 95%, or 99%. In certain embodiments, the suppression of the accumulation of the protein is in an amount sufficient to cause a therapeutic effect, e.g., to reduce the formation of tangles.

The present invention provides a method of preventing cytotoxic effects of mutant huntingtin in a cell by introducing nucleic acid molecules (e.g., a ribonucleic acid (RNA)) described herein into the cell in an amount sufficient to suppress accumulation of huntingtin. In certain embodiments, the nucleic acid molecules prevents cytotoxic effects of huntingtin, e.g., in a neuronal cell.

The present invention provides a method to inhibit expression of a huntingtin gene in a cell by introducing a nucleic acid molecule (e.g., a ribonucleic acid (RNA)) described herein into the cell in an amount sufficient to inhibit expression of the huntingtin, and wherein the RNA inhibits expression of the huntingtin gene. In certain embodiments, the huntingtin is inhibited by at least 10%, 20%, 30%, 40%, 50%, 60%, 70%, 80%, 90% 95%, or 99%.

The present invention provides a method to inhibit expression of a huntingtin gene in a mammal (e.g., a human or a non-human mammal) by (a) providing a mammal containing a neuronal cell, wherein the neuronal cell contains the huntingtin gene and the neuronal cell is susceptible to RNA interference, and the huntingtin gene is expressed in the neuronal cell; and (b) contacting the mammal with a ribonucleic acid (RNA) or a vector described herein, thereby inhibiting expression of the huntingtin gene. In certain embodiments, the accumulation of huntingtin is suppressed by at least 10%. In certain embodiments, the huntingtin is inhibited by at least 10%, 20%, 30%, 40%, 50%, 60%, 70%, 80%, 90% 95%, or 99%. In certain embodiments, the cell is located in vivo in a mammal.

The present invention provides a viral vector comprising a promoter and a micro RNA (miRNA) shuttle containing an embedded siRNA specific for a target sequence. In certain embodiments, the promoter is an inducible promoter. In certain embodiments, the vector is an adenoviral, lentiviral, adeno-associated viral (AAV), poliovirus, HSV, or murine Maloney-based viral vector. In certain embodiments, the targeted sequence is a sequence associated with Huntington's Disease. The target sequence, in certain embodiments, is a sequence encoding huntingtin.

The present invention provides a method of preventing cytotoxic effects of neurodegenerative disease in a mammal in need thereof, by introducing the vector encoding a miRNA described herein into a cell in an amount sufficient to suppress accumulation of a protein associated with Huntington's Disease, and wherein the RNA prevents cytotoxic effects of Huntington's Disease (also referred to as HD, and the protein involved is huntingtin, also called htt).

The present invention also provides a method to inhibit expression of a protein associated with Huntington's Disease in a mammal in need thereof, by introducing the vector encoding a miRNA described herein into a cell in an amount sufficient to inhibit expression of the huntingtin protein, wherein the RNA inhibits expression of the huntingtin protein. The huntingtin protein is inhibited by at least 10%, 20%, 30%, 40%, 50%, 60%, 70%, 80%, 90% 95%, or 99%.

This invention relates to compounds, compositions, and methods useful for modulating Huntington's Disease gene expression using short interfering nucleic acid (siRNA) molecules. This invention also relates to compounds, compositions, and methods useful for modulating the expression and activity of other genes involved in pathways of HD gene expression and/or activity by RNA interference (RNAi) using small nucleic acid molecules. In particular, the instant invention features small nucleic acid molecules, such as short interfering nucleic acid (siNA), short interfering RNA (siRNA), double-stranded RNA (dsRNA), micro-RNA (miRNA), and short hairpin RNA (shRNA) molecules and methods used to modulate the expression HD genes. A siRNA molecule of the instant invention can be, e.g., chemically synthesized, expressed from a vector or enzymatically synthesized.

As used herein when a claim indicates an RNA "corresponding to" it is meant the RNA that has the same sequence as the DNA, except that uracil is substituted for thymine.

The present invention further provides a method of substantially silencing a target gene of interest or targeted allele for the gene of interest in order to provide a therapeutic effect. As used herein the term "substantially silencing" or "substantially silenced" refers to decreasing, reducing, or inhibiting the expression of the target gene or target allele by at least about 5%, 10%, 15%, 20%, 25%, 30%, 35%, 40%, 45%, 50%, 55%, 60%, 65%, 70%, 75%, 80%, 85% to 100%. As used herein the term "therapeutic effect" refers to a change in the associated abnormalities of the disease state, including pathological and behavioral deficits; a change in the time to progression of the disease state; a reduction, lessening, or alteration of a symptom of the disease; or an improvement in the quality of life of the person afflicted with the disease. Therapeutic effects can be measured quantitatively by a physician or qualitatively by a patient afflicted with the disease state targeted by the siRNA. In certain embodiments wherein both the mutant and wild type allele are substantially silenced, the term therapeutic effect defines a condition in which silencing of the wild type allele's expression does not have a deleterious or harmful effect on normal functions such that the patient would not have a therapeutic effect.

In one embodiment, the invention features a method for treating or preventing Huntington's Disease in a subject or organism comprising contacting the subject or organism with a siRNA of the invention under conditions suitable to modulate the expression of the HD gene in the subject or organism whereby the treatment or prevention of Huntington's Disease can be achieved. In one embodiment, the HD gene target comprises both HD allele (e.g., an allele comprising a trinucleotide (CAG) repeat expansion and a wild type allele). The siRNA molecule of the invention can be expressed from vectors as described herein or otherwise known in the art to target appropriate tissues or cells in the subject or organism.

In one embodiment, the invention features a method for treating or preventing Huntington's Disease in a subject or organism comprising, contacting the subject or organism with a siRNA molecule of the invention via local administration to relevant tissues or cells, such as brain cells and tissues (e.g., basal ganglia, striatum, or cortex), for example, by administration of vectors or expression cassettes of the invention that provide siRNA molecules of the invention to relevant cells (e.g., basal ganglia, striatum, or cortex). In one embodiment, the siRNA, vector, or expression cassette is administered to the subject or organism by stereotactic or convection enhanced delivery to the brain. For example, U.S. Pat. No. 5,720,720 provides methods and devices useful for stereotactic and convection enhanced delivery of reagents to the brain. Such methods and devices can be readily used for the delivery of siRNAs, vectors, or expression cassettes of the invention to a subject or organism, and is U.S. Pat. No. 5,720,720 is incorporated by reference herein in its entirety. US Patent Application Nos. 2002/0141980; 2002/0114780; and 2002/0187127 all provide methods and devices useful for stereotactic and convection enhanced delivery of reagents that can be readily adapted for delivery of siRNAs, vectors, or expression cassettes of the invention to a subject or organism, and are incorporated by reference herein in their entirety. Particular devices that may be useful in delivering siRNAs, vectors, or expression cassettes of the invention to a subject or organism are for example described in US Patent Application No. 2004/0162255, which is incorporated by reference herein in its entirety. The siRNA molecule of the invention can be expressed from vectors as described herein or otherwise known in the art to target appropriate tissues or cells in the subject or organism.

Methods of delivery of viral vectors include, but are not limited to, intra-arterial, intra-muscular, intravenous, intra-nasal and oral routes. Generally, AAV virions may be introduced into cells of the CNS using either in vivo or in vitro transduction techniques. If transduced in vitro, the desired recipient cell will be removed from the subject, transduced with AAV virions and reintroduced into the subject. Alternatively, syngeneic or xenogeneic cells can be used where those cells will not generate an inappropriate immune response in the subject.

Suitable methods for the delivery and introduction of transduced cells into a subject have been described. For example, cells can be transduced in vitro by combining recombinant AAV virions with CNS cells e.g., in appropriate media, and screening for those cells harboring the DNA of interest can be screened using conventional techniques such as Southern blots and/or PCR, or by using selectable markers. Transduced cells can then be formulated into pharmaceutical compositions, described more fully below, and the composition introduced into the subject by various techniques, such as by grafting, intramuscular, intravenous, subcutaneous and intraperitoneal injection.

In one embodiment, for in vivo delivery, AAV virions are formulated into pharmaceutical compositions and will generally be administered parenterally, e.g., by intramuscular injection directly into skeletal or cardiac muscle or by injection into the CNS.

In one embodiment, viral vectors of the invention are delivered to the CNS via convection-enhanced delivery (CED) systems that can efficiently deliver viral vectors, e.g., AAV, over large regions of a subject's brain (e.g., striatum and/or cortex). As described in detail and exemplified below, these methods are suitable for a variety of viral vectors, for instance AAV vectors carrying therapeutic genes (e.g., siRNAs).

Any convection-enhanced delivery device may be appropriate for delivery of viral vectors. In one embodiment, the device is an osmotic pump or an infusion pump. Both osmotic and infusion pumps are commercially available from a variety of suppliers, for example Alzet Corporation, Hamilton Corporation, Aiza, Inc., Palo Alto, Calif.). Typically, a viral vector is delivered via CED devices as follows. A catheter, cannula or other injection device is inserted into CNS tissue in the chosen subject. In view of the teachings herein, one of skill in the art could readily determine which general area of the CNS is an appropriate target. For example, when delivering AAV vector encoding a therapeutic gene to treat HD, the striatum is a suitable area of the brain to target. Stereotactic maps and positioning devices are available, for example from ASI Instruments, Warren, Mich. Positioning may also be conducted by using anatomical maps obtained by CT and/or MRI imaging of the subject's brain to help guide the injection device to the chosen target. Moreover, because the methods described herein can be practiced such that relatively large areas of the brain take up the viral vectors, fewer infusion cannula are needed. Since surgical complications are related to the number of penetrations, the methods described herein also serve to reduce the side effects seen with conventional delivery techniques.

In one embodiment, pharmaceutical compositions will comprise sufficient genetic material to produce a therapeutically effective amount of the siRNA of interest, i.e., an amount sufficient to reduce or ameliorate symptoms of the disease state in question or an amount sufficient to confer the desired benefit. The pharmaceutical compositions may also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, sorbitol, Tween80, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in REMINGTON'S PHARMACEUTICAL SCIENCES (Mack Pub. Co., N.J. 1991).

As is apparent to those skilled in the art in view of the teachings of this specification, an effective amount of viral vector which must be added can be empirically determined. Administration can be effected in one dose, continuously or intermittently throughout the course of treatment. Methods of determining the most effective means and dosages of administration are well known to those of skill in the art and will vary with the viral vector, the composition of the therapy, the target cells, and the subject being treated. Single and multiple administrations can be carried out with the dose level and pattern being selected by the treating physician.

It should be understood that more than one transgene could be expressed by the delivered viral vector. Alternatively, separate vectors, each expressing one or more different transgenes, can also be delivered to the CNS as described herein. Furthermore, it is also intended that the viral vectors delivered by the methods of the present invention be combined with other suitable compositions and therapies.

The present invention further provides an miRNA or shRNA, an expression cassette and/or a vector as described herein for use in medical treatment or diagnosis.

The present invention provides the use of an miRNA or shRNA, an expression cassette and/or a vector as described herein to prepare a medicament useful for treating a condition amenable to RNAi in an animal, e.g., useful for treating Huntington's Disease.

The present invention also provides a nucleic acid, expression cassette, vector, or composition of the invention for use in therapy.

The present invention also provides a nucleic acid, expression cassette, vector, or composition of the invention for treating, e.g., for use in the prophylactic or therapeutic treatment of, Huntington's Disease.

In certain embodiments, the agent is administered to the brain of the subject. In certain embodiments, the agent is administered either directly to the brain or via the bloodstream. In certain embodiments, the therapeutic agent is administered intra-cranially. In certain embodiments, the therapeutic agent is administered to the subject's cisterna magna, striatum, cortex or ventricle, subarachnoid space and/or intrathecal space. In certain embodiments, the subject is human. In certain embodiments, the subject is a non-human mammal. In certain embodiments, the agent is injected at 1-5 locations in the brain, such as at one, two, or three locations in the brain. In certain embodiments, the method further comprises additionally administering the rAAV to the non-human primate's brain ventricle, subarachnoid space and/or intrathecal space. More specifically, the present invention provides a method of delivering a nucleic acid to a cell with contact to the circulating CSF, such as an ependymal cell, a pial cell, meningeal cell, a brain endothelial cell, comprising administering to the cell an AAV particle containing a vector comprising the nucleic acid inserted between a pair of AAV inverted terminal repeats, thereby delivering the nucleic acid to the cell.

The present invention also provides a method of contacting a cell with the nucleic acid, the expression cassette, the vector, or the duplex described herein, so as to treat the Huntington's Disease, wherein the cell is an ependymal, pial, endothelial, brain ventricle, and/or meningeal cell.

BRIEF DESCRIPTION OF THE FIGURES

FIGS. 2A-2D: Characterization of miHDS1 off-target genes. a) List of genes among the 25 percentile of predicted miHDS1 off target genes. Information displayed: Gene ID, Reference sequence, miRNA binding site type, nucleotide 3'UTR position, predicted target scan context score, ddG score predicted by PITA algorithm. b) Cartoon depicting miHDS1:mRNA binding sites (miHDS1 is SEQ ID NO: 1) on predicted off-targeted genes (Bcl2 is SEQ ID NO:31; Smad9 is SEQ ID NO:32; Sdf4 is SEQ ID NO:33; Map2k6 is SEQ ID NO:34). c) Quantitative Q-PCR analysis of Htt, Bcl2, Smad9, Sdf4 and Map2k6 mRNA levels in striatum samples 4 months after miHDS1 injection. All samples were normalized to β-actin and results are the mean±sem relative to mice injected with miCt1. (n=6 mice per group; *p<0.05, p<0.01, Mann Whitney Test) d) Quantitative Q-PCR analysis of Ht, Bcl2, Smad9, Sdf4 and Map2k6 mRNA levels in SthdhQ7 cells after miHDS1 electroporation. All samples were normalized to β-actin and results are the mean±sem relative to cells electroporated with plasmid containing U6 promoter or miCt1 expression cassette. (n=8 electroporated wells; p<0.01, One way ANOVA followed by a Bonferroni's Post-test)

FIGS. 3A-3C: Generation of single nucleotide miHDS1 seed variants. a) Cartoon depicting location of single nucleotide modifications in the seed region of miHDS1 sequence (Pri-miHDS1 is SEQ ID NO:4; Pre-miHDS1 is SEQ ID NO:5; RISC loaded miRNA sequence is SEQ ID NO: 1). b) Impact on SPS score depending on the position of nucleotide mismatch over miHDS1 off targets. c) Table indicates the number of predicted off-target genes (overall and Striatum specific) for miHDS1 and miHDS1-variants, as well as the number of shared off-targets.

FIGS. 4A-4I: Silencing efficacy of single nucleotide miHDS1 seed variants. a) Quantitative analysis of hHtt mRNA levels in HEK293 cells transfected with U6/miHDS1 expression cassettes. Total RNA was collected 24 hours post-transfection and hHtt levels were determined by Q-PCR. All samples were normalized to β-actin and results are the mean±sem relative to cells transfected with miCt1 (n=12 wells; p<0.01, *p<0.001, One way ANOVA followed by a Bonferroni's Post-test). b) miHDS1, miHDS1v5u, miHDS1v6a and miHDS1v7u expression cassettes were transfected into human HEK293 cells, and endogenous huntingtin protein levels were determined 48 hours after transfection. miCt1 was used as a no silencing control and β-Catenin serves as a loading control. c) Quantification of hHtt protein levels 48 hours after transfection of miHDS1, miHDS1v5u, miHDS1v6a and miHDS1v7u. Data is the mean±sem relative to cells transfected with miCt1 (n=6, three different western blots, *p<0.01, Mann Whitney Test). d) miHDS1v5u and miHDS1 v6a pairing to mouse huntingtin mRNA (miHDS1v5U is SEQ ID NO:6; Mouse Htt is SEQ ID NO:2; miHDS1v6A is SEQ ID NO:7). e) miHDS1, miHDS1v5u, and miHDS1v6a expression cassettes were electroporated into mouse SthdhQ7 cells, and endogenous huntingtin protein levels were determined 48 hours after electroporation. miCt1 was used as a no silencing control and β-Catenin serves as a loading control. f) Quantification of mHtt protein levels 48 hours after electroporation of miHDS1, miHDS1v5u and miHDS1v6a. Data is the mean±sem relative to cells transfected with miCt1 (n=6, three different western blots, *p<0.01, Mann Whitney Test). g-h-i) Quantitative analysis of mHtt, Bcl2 and Smad9 mRNA levels in SthdhQ7 cells electroporated with U6/miHDS1, U6/miHDS1 v5u and U6/miHDS1 v6a expression cassettes. Total RNA was collected 24 hours post-electroporation and mHtt, Bcl2 and Smad9 levels were determined by Q-PCR. All samples were normalized to β-actin and results are the mean±sem relative to cells transfected with U6 containing promoter and U6/miCt1 expression cassette (n=12 wells; #p<0.01, One way ANOVA followed by a Bonferroni's Post-test).

FIGS. 5A-5F: Generation of miHDss1-4 sequences to target human huntingtin expression. a). Four artificial miRNA trigger containing miCt1 seed sequence were generated allowing a single nucleotide mismatch between seed region and targeted human Htt mRNA. MiHDss1 and miHDss4 binding sites are located at the 3'UTR, whereas miHDss2 and 3 bind at exon 7-8 boundary and exon 33 of the hHtt mRNA, respectively. b) miRNA/mRNA binding pair between miHDss1-4 and human huntingtin mRNA. Single nucleotide mismatches where found at the seed region position 7, 6, 5 and 4 for miHDss1, 2, 3 and 4 sequences, respectively (miHDss1 is SEQ ID NO:35; miHDss2 is SEQ ID NO:36; miHDss3 is SEQ ID NO:37; miHDss4 is SEQ ID NO:38). Figure also discloses SEQ ID NOS 40-43, respectively, in order of appearance. c) Quantitative analysis of hHtt mRNA levels in HEK293 cells transfected with U6/miHDss1-4 expression cassettes. Total RNA was collected 24 hours post-transfection and hHtt levels were determined by Q-PCR. All samples were normalized to β-actin and results are the mean±sem relative to cells transfected with miCt1 (n=8 wells; *p<0.001, One way ANOVA followed by a Bonferroni's Post-test). d) miHDss3 expression cassette was transfected into human HEK293 cells, and endogenous huntingtin protein levels were determined 48 hours after transfection. miCt1 was used as a no silencing control and β-Catenin serves as a loading control. e) Quantification of hHtt protein levels 48 hours after transfection of miHDss3. Data is the mean±sem relative to cells transfected with miCt1 (n=6, two different western blots, *p<0.01, Mann Whitney Test). f) The PITA algorithm was used to determine binding stability of miHDss3 (SEQ ID NO:37) and miCt1 (SEQ ID NO:39) over predicted unintended mRNA binding sites. Seed region of miCt1 and miHDss3 are highlighted in bold. Data is shown as a ddG (Kcal/mol) score for each off target gene with respect miCt1 or miHDss3. Our prediction suggests the 3' sequence of miHDss3 provide more binding stability over off-target genes than miCt1.

FIGS. 6A-6E: In vivo tolerability of miHDS1-variants and miHDss3 sequences. a) Experimental strategy to evaluate in vivo tolerability of new miRNA sequences design. b) Cartoon depicting AAV/stuffer shuttle vectors containing miHDS1 variants and miHDss3 expression cassettes. c) Rotarod data from mice injected with Formulation buffer (n=7), miCt1 (n=8), miHDS1 (n=9), miHDS1v5u (n=10), miHDS1v6a (n=11) or miHDss3 (n=10). Data is displayed as the average of the best 2 trials of each mouse per day of the four consecutive days tested at 7 weeks (Basal), 16 weeks and 24 weeks. Latency to fall is shown as mean±s.e.m Relative to mice injected with miCt1. ($*p<0.05$, One way ANOVA followed by a Bonferroni's Post-test). d) Weight gain analysis of mice injected with Formulation buffer, miCt1, miHDS1, miHDS1v5u, miHDS1v6a or miHDss3. Data is shown as increase weight respect to basal time point at 7 weeks. e) Clasping analysis of mice injected with miHDs1 and miCt1. Data is shown as percentage and number of mice showing clasping at the indicated time points

DETAILED DESCRIPTION OF THE INVENTION

Figure 1:
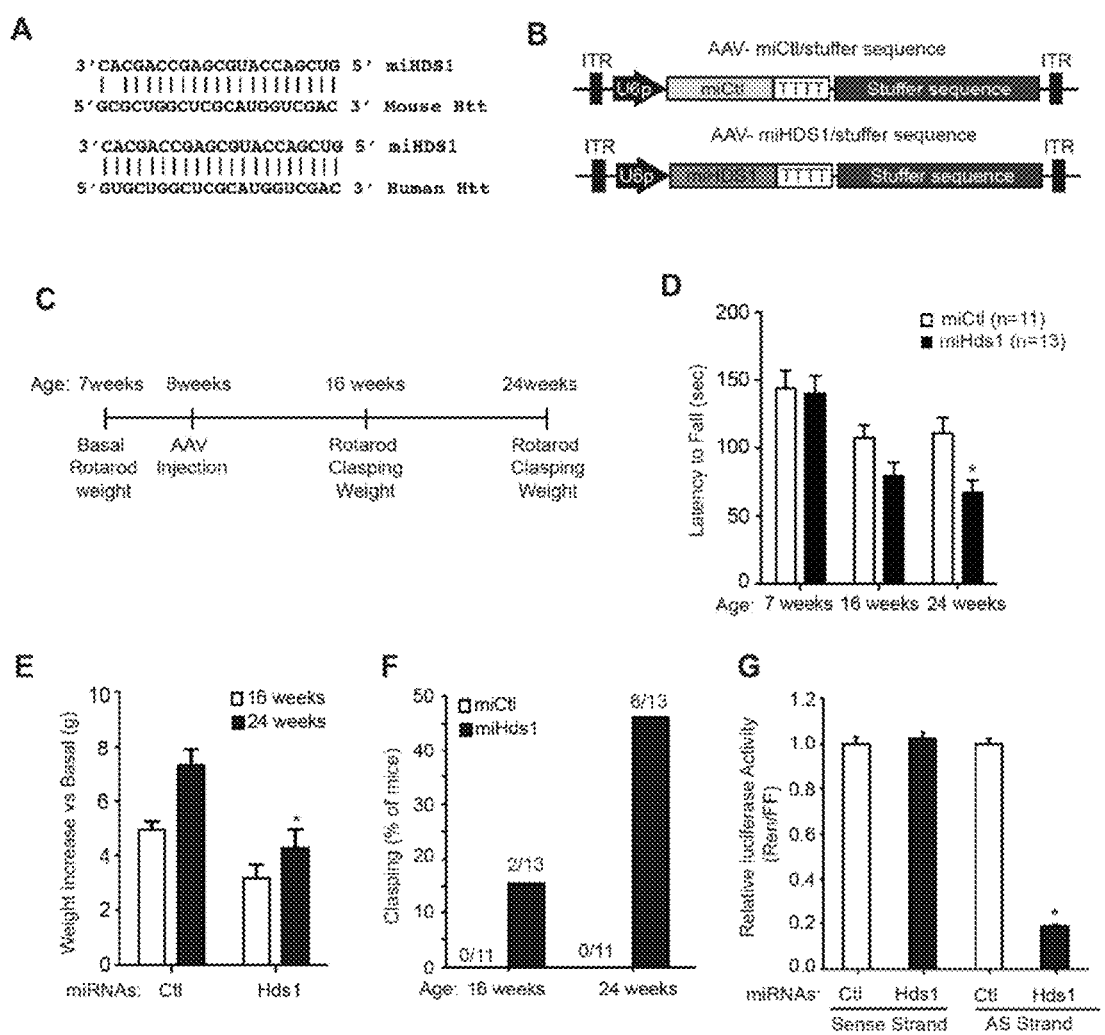
FIGS. 1A-1G: Overexpression of miHDS1 causes adverse effects in the mouse brain. a) miHDS1 pairing to mouse and human huntingtin mRNA (miHDS1 is SEQ ID NO:1; mouse Htt is SEQ ID NO:2; and human Htt is SEQ ID NO:3). b) Cartoon depicting AAV/stuffer shuttle vectors containing miHDS1 and miCt1 expression cassettes. c) Experimental strategy to evaluate miHDS1 in vivo tolerability. d) Rotarod data from mice injected with miHDS1 (n=13) or miCt1 (n=11). Data is displayed as the average of the best 2 trials of each mouse per day of the four consecutive days tested at 7 weeks (Basal), 16 weeks and 24 weeks. Latency to fall is shown as mean±s.e.m. (*p>0.05, unpaired t-test at the indicated times). e) Weight gain analysis of mice injected with miHDS1 and miCt1. Data is shown as increase weight respect to basal time point at 7 weeks. f) Clasping analysis of mice injected with miHds1 and miCt1. Data is shown as percentage and number of mice showing clasping at the indicated time points. g) Strand biasing of U6/miHDS1 vector. Strand biasing was assessed measuring luciferase activity from reporter constructs containing target sequences complementary to the passenger (sense) or guide (antisense) miHDS1 strands. Results are a representative experiment of 3 different experiments (n=4/group). Data is shown as mean±sem relative to cells tranfected with miCt1 and demonstrate that miHDS1 preferentially loads the guide miHDS1 strand.

RNA Interference (RNAi) is a process of gene regulation mediated by small dsRNAs. RNAi is used as a common biological tool to study gene function, and is under investigation as a therapeutic to treat various diseases. RNAi delivery or expression can be through the administration of exogenous siRNAs (transient gene silencing) or through the administration of vectors expressing stem-loop RNAs (persistent gene silencing). The absolute specificity of RNAi is questionable. Issues that must be addressed include cellular responses to dsRNA (IFN-b, PKR, OAS1) and off-target effects due to saturation of RNAi machinery or via partial complementarity with unintended mRNAs. There is an on-going need for optimizing RNAi vectors and potentially developing tissue-specific and regulated expression strategies The use of RNAi as a therapeutic is dependent upon the elucidation of several factors including i) the delivery and persistence of the RNAi construct for effective silencing of the target gene sequence; ii) the design of the siRNA in order to achieve effective knock down or gene suppression of the target sequence, and iii) the optimal siRNA expression system (shRNA or miRNA) for delivery of the therapeutic siRNA. While many studies have evaluated the use of RNAi delivered as chemically synthesized oligonucleotide structures, for many clinical conditions and disease states such as Huntington's Disease, it is believed that to achieve therapeutic benefit there is a need for long term and or persistent high level expression of the therapeutic siRNA as achieved by endogenous production of expressed siRNA. To date, shRNA- and artificial miRNA-based strategies have been compared with conflicting results. The therapeutic utility of expressed RNAi is unresolved due to safety concerns as a result of off target toxicity arising from cellular responses to dsRNA (IFN-b, PKR, OAS1), saturation of RNAi machinery or silencing of off targets via partial complementarity with unintended mRNAs. Thus, there is an on-going need for optimizing expressed RNAi vectors that are safe and effective.

shRNAs are comprised of stem-loop structures which are designed to contain a 5' flanking region, siRNA region segments, a loop region, a 3' siRNA region and a 3' flanking region. Most RNAi expression strategies have utilized short-hairpin RNAs (shRNAs) driven by strong polIII-based promoters. Many shRNAs have demonstrated effective knock down of the target sequences in vitro as well as in vivo, however, some shRNAs which demonstrated effective knock down of the target gene were also found to have toxicity in vivo. A recently discovered alternative approach is the use of artificial miRNAs (pri-miRNA scaffolds shuttling siRNA sequences) as RNAi vectors. Artificial miRNAs more naturally resemble endogenous RNAi substrates and are more amenable to Pol-II transcription (e.g., allowing tissue-specific expression of RNAi) and polycistronic strategies (e.g., allowing delivery of multiple siRNA sequences). To date the efficacy of miRNA based vector systems compared to shRNA has been confounded by conflicting results. Importantly, the question of off-target toxicity produced by the two systems has not been evaluated.

An important consideration for development of expressed siRNA is the concept of "dosing" the host cell with the expressed siRNA construct. "Dosing" for an expressed siRNA in the context of the present invention refers to and can be dependent on the delivery vehicle (e.g., viral or nonviral), the relative amounts or concentration of the delivery vehicle, and the strength and specificity of the promoter utilized to drive the expression of the siRNA sequence.

The inventors have developed artificial miRNA shuttle vectors that incorporate the stem loop sequences contained in shRNAs within modifications of a naturally occurring human microRNA 30 sequence or mi30 sequence that serve to shuttle these small interfering RNA (siRNA) sequences. See, e.g., PCT Publication WO 2008/150897, which is incorporated by reference herein.

The inventors have developed artificial miRNAs, pri-miRNAs, pre-miRNAs, expression vectors, duplexes, and methods for treating Huntington's disease. See, e.g., PCT Publication WO 2012/109667, which is incorporated by reference herein.

MicroRNA Shuttles for RNAi miRNAs are small cellular RNAs (~22 nt) that are processed from precursor stem loop transcripts. Known miRNA stem loops can be modified to contain RNAi sequences specific for genes of interest. miRNA molecules can be preferable over shRNA molecules because miRNAs are endogenously expressed. Therefore, miRNA molecules are unlikely to induce dsRNA-responsive interferon pathways, they are processed more efficiently than shRNAs, and they have been shown to silence 80% more effectively.

Also, the promoter roles are different for miRNA molecules as compared to shRNA molecules. Tissue-specific, inducible expression of shRNAs involves truncation of polII promoters to the transcription start site. In contrast, miRNAs can be expressed from any polII promoter because the transcription start and stop sites can be relatively arbitrary.

Treatment of Huntington's Disease

The dominant polyglutamine expansion diseases, which include Spinocerebellar ataxia type 1 (SCA1) and Huntington's disease (HD), are progressive, untreatable neurodegenerative disorders. In inducible mouse models HD, repression of mutant allele expression improves disease phenotypes. Thus, therapies designed to inhibit disease gene expression would be beneficial. The present invention provides methods of using RNAi in vivo to treat Huntington's Disease. "Treating" as used herein refers to ameliorating at least one symptom of, curing and/or preventing the development of a disease or a condition.

In certain embodiment of the invention, RNAi molecules are employed to inhibit expression of a target gene. By "inhibit expression" is meant to reduce, diminish or suppress expression of a target gene. Expression of a target gene may be inhibited via "gene silencing." Gene silencing refers to the suppression of gene expression, e.g., transgene, heterologous gene and/or endogenous gene expression, which may be mediated through processes that affect transcription and/or through processes that affect post-transcriptional mechanisms. In some embodiments, gene silencing occurs when an RNAi molecule initiates the inhibition or degradation of the mRNA transcribed from a gene of interest in a sequence-specific manner via RNA interference, thereby preventing translation of the gene's product.

The reference to siRNAs herein is meant to include shRNAs and other small RNAs that can or are capable of modulating the expression of a targeted gene, e.g., the HD gene, for example via RNA interference. Such small RNAs include without limitation, shRNAs and miroRNAs (miR-NAs).

Disclosed herein is a strategy that results in substantial silencing of targeted genes via RNAi. Use of this strategy results in markedly diminished in vitro and in vivo expression of targeted genes. This strategy is useful in reducing expression of targeted genes in order to model biological processes or to provide therapy for human diseases. For example, this strategy can be applied to Huntington's Disease. As used herein the term "substantial silencing" means that the mRNA of the targeted gene is inhibited and/or degraded by the presence of the introduced siRNA, such that expression of the targeted gene is reduced by about 10% to 100% as compared to the level of expression seen when the siRNA is not present. Generally, when an gene is substantially silenced, it will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, 98%, 99% or even 100% reduction expression as compared to when the siRNA is not present. As used herein the term "substantially normal activity" means the level of expression of a gene when an siRNA has not been introduced to a cell.

Huntington disease (HD) is a strong candidate for siRNA-based therapy. HD is caused by CAG repeat expansions that encode polyQ in the disease protein. PolyQ expansion confers a dominant toxic property on the mutant protein that is associated with aberrant accumulation of the disease protein in neurons. HD is progressive, ultimately fatal disorders that typically begin in adulthood. Expansion of the CAG repeat/polyQ domain confers upon the encoded protein a dominant toxic property. Thus, as a therapeutic strategy, efforts to lower expression of the mutant gene product prior to cell death could be highly beneficial to patients.

RNA Interference (RNAi) Molecules

An "RNA interference," "RNAi," "small interfering RNA" or "short interfering RNA" or "siRNA" or "short hairpin RNA" or "shRNA" molecule, or "miRNA" is a RNA duplex of nucleotides that is targeted to a nucleic acid sequence of interest, for example, huntingtin (htt). As used herein, the term "siRNA" is a generic term that encompasses the subset of shRNAs and miRNAs. An "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In certain embodiments, the siRNAs are targeted to the sequence encoding ataxin-1 or huntingtin. In some embodiments, the length of the duplex of siRNAs is less than 30 base pairs. In some embodiments, the duplex can be 29, 28, 27, 26, 25, 24, 23, 22, 21, 20, 19, 18, 17, 16, 15, 14, 13, 12, 11 or 10 base pairs in length. In some embodiments, the length of the duplex is 19 to 25 base pairs in length. In certain embodiment, the length of the duplex is 19 or 21 base pairs in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12, 13, 14, 15, 16, 17, 18, 19, 20, 21, 22, 23, 24 or 25 nucleotides in length. In certain embodiments, the loop is 18 nucleotides in length. The hairpin structure can also contain 3' and/or 5' overhang portions. In some embodiments, the overhang is a 3' and/or a 5' overhang 0, 1, 2, 3, 4 or 5 nucleotides in length.

The transcriptional unit of a "shRNA" is comprised of sense and antisense sequences connected by a loop of unpaired nucleotides. shRNAs are exported from the nucleus by Exportin-5, and once in the cytoplasm, are processed by Dicer to generate functional siRNAs. "miRNAs" stem-loops are comprised of sense and antisense sequences connected by a loop of unpaired nucleotides typically expressed as part of larger primary transcripts (pri-miRNAs), which are excised by the Drosha-DGCR8 complex generating intermediates known as pre-miRNAs, which are subsequently exported from the nucleus by Exportin-5, and once in the cytoplasm, are processed by Dicer to generate functional siRNAs. "Artificial miRNA" or an "artificial miRNA shuttle vector," as used herein interchangably, refers to a primary miRNA transcript that has had a region of the duplex stem loop (at least about 9-20 nucleotides) which is excised via Drosha and Dicer processing replaced with the siRNA sequences for the target gene while retaining the structural elements within the stem loop necessary for effective Drosha processing. The term "artificial" arises from the fact the flanking sequences (~35 nucleotides upstream and ~40 nucleotides downstream) arise from restriction enzyme sites within the multiple cloning site of the siRNA. As used herein the term "miRNA" encompasses both the naturally occurring miRNA sequences as well as artificially generated miRNA shuttle vectors.

The siRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal or a sequence of six Ts.

"Off-target toxicity" refers to deleterious, undesirable, or unintended phenotypic changes of a host cell that expresses or contains an siRNA. Off-target toxicity may result in loss of desirable function, gain of non-desirable function, or even death at the cellular or organismal level. Off-target toxicity may occur immediately upon expression of the siRNA or may occur gradually over time. Off-target toxicity may occur as a direct result of the expression siRNA or may occur as a result of induction of host immune response to the cell expressing the siRNA. Without wishing to be bound by theory, off-target toxicity is postulated to arise from high levels or overabundance of RNAi substrates within the cell. These overabundant or overexpressed RNAi substrates, including without limitation pre- or pri RNAi substrates as well as overabundant mature antisense-RNAs, may compete for endogenous RNAi machinery, thus disrupting natural miRNA biogenesis and function. Off-target toxicity may also arise from an increased likelihood of silencing of unintended mRNAs (i.e., off-target) due to partial complementarity of the sequence. Off target toxicity may also occur from improper strand biasing of a non-guide region such that there is preferential loading of the non-guide region over the targeted or guide region of the RNAi. Off-target toxicity may also arise from stimulation of cellular responses to dsRNAs which include dsRNA (IFN-b, PKR, OAS1). "Decreased off target toxicity" refers to a decrease, reduction, abrogation or attenuation in off target toxicity such that the therapeutic effect is more beneficial to the host than the toxicity is limiting or detrimental as measured by an improved duration or quality of life or an improved sign or symptom of a disease or condition being targeted by the siRNA. "Limited off target toxicity" or "low off target toxicity" is used to refer to an unintended undesirable phenotypic changes to a cell or organism, whether detectable or not, that does not preclude or outweigh or limit the therapeutic benefit to the host treated with the siRNA and may be considered a "side effect" of the therapy. Decreased or limited off target toxicity may be determined or inferred by comparing the in vitro analysis such as Northern blot or QPCR for the levels of siRNA substrates or the in vivo effects comparing an equivalent shRNA vector to the miRNA shuttle vector of the present invention.

"Knock-down," "knock-down technology" refers to a technique of gene silencing in which the expression of a target gene is reduced as compared to the gene expression prior to the introduction of the siRNA, which can lead to the inhibition of production of the target gene product. The term "reduced" is used herein to indicate that the target gene expression is lowered by 1-100%. In other words, the amount of RNA available for translation into a polypeptide or protein is minimized. For example, the amount of protein may be reduced by 10, 20, 30, 40, 50, 60, 70, 80, 90, 95, or 99%. In some embodiments, the expression is reduced by about 90% (i.e., only about 10% of the amount of protein is observed a cell as compared to a cell where siRNA molecules have not been administered). Knock-down of gene expression can be directed by the use of dsRNAs or siRNAs.

"RNA interference (RNAi)" is the process of sequence-specific, post-transcriptional gene silencing initiated by siRNA. During RNAi, siRNA induces degradation of target mRNA with consequent sequence-specific inhibition of gene expression.

According to a method of the present invention, the expression of huntingtin can be modified via RNAi. For example, the accumulation of huntingtin can be suppressed in a cell. The term "suppressing" refers to the diminution, reduction or elimination in the number or amount of transcripts present in a particular cell. For example, the accumulation of mRNA encoding huntingtin can be suppressed in a cell by RNA interference (RNAi), e.g., the gene is silenced by sequence-specific double-stranded RNA (dsRNA), which is also called short interfering RNA (siRNA). These siRNAs can be two separate RNA molecules that have hybridized together, or they may be a single hairpin wherein two portions of a RNA molecule have hybridized together to form a duplex.

A mutant protein refers to the protein encoded by a gene having a mutation, e.g., a missense or nonsense mutation in huntingtin. A mutant huntingtin may be disease-causing, i.e., may lead to a disease associated with the presence of huntingtin in an animal having either one or two mutant allele(s).

The term "gene" is used broadly to refer to any segment of nucleic acid associated with a biological function. Thus, genes include coding sequences and/or the regulatory sequences required for their expression. For example, "gene" refers to a nucleic acid fragment that expresses mRNA, functional RNA, or specific protein, including regulatory sequences. "Genes" also include nonexpressed DNA segments that, for example, form recognition sequences for other proteins. "Genes" can be obtained from a variety of sources, including cloning from a source of interest or synthesizing from known or predicted sequence information, and may include sequences designed to have desired parameters. An "allele" is one of several alternative forms of a gene occupying a given locus on a chromosome.

The term "nucleic acid" refers to deoxyribonucleic acid (DNA) or ribonucleic acid (RNA) and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues. A "nucleic acid fragment" is a portion of a given nucleic acid molecule.

A "nucleotide sequence" is a polymer of DNA or RNA that can be single-stranded or double-stranded, optionally containing synthetic, non-natural or altered nucleotide bases capable of incorporation into DNA or RNA polymers.

The terms "nucleic acid," "nucleic acid molecule," "nucleic acid fragment," "nucleic acid sequence or segment," or "polynucleotide" are used interchangeably and may also be used interchangeably with gene, cDNA, DNA and RNA encoded by a gene.

The invention encompasses isolated or substantially purified nucleic acid nucleic acid molecules and compositions containing those molecules. In the context of the present invention, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. Fragments and variants of the disclosed nucleotide sequences are also encompassed by the present invention. By "fragment" or "portion" is meant a full length or less than full length of the nucleotide sequence.

"Naturally occurring," "native," or "wild-type" is used to describe an object that can be found in nature as distinct from being artificially produced. For example, a protein or nucleotide sequence present in an organism (including a virus), which can be isolated from a source in nature and that has not been intentionally modified by a person in the laboratory, is naturally occurring.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of molecular biology techniques, as, for example, with polymerase chain reaction (PCR) and hybridization techniques. Variant nucleotide sequences also include synthetically derived nucleotide sequences, such as those generated, for example, by using site-directed mutagenesis, which encode the native protein, as well as those that encode a polypeptide having amino acid substitutions. Generally, nucleotide sequence variants of the invention will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

A "transgene" refers to a gene that has been introduced into the genome by transformation. Transgenes include, for example, DNA that is either heterologous or homologous to the DNA of a particular cell to be transformed. Additionally, transgenes may include native genes inserted into a non-native organism, or chimeric genes.

The term "endogenous gene" refers to a native gene in its natural location in the genome of an organism.

The terms "protein," "peptide" and "polypeptide" are used interchangeably herein.

"Wild-type" refers to the normal gene or organism found in nature.

"Genome" refers to the complete genetic material of an organism.

A "vector" is defined to include, inter alia, any viral vector, as well as any plasmid, cosmid, phage or binary vector in double or single stranded linear or circular form that may or may not be self-transmissible or mobilizable, and that can transform prokaryotic or eukaryotic host either by integration into the cellular genome or exist extrachromosomally (e.g., autonomous replicating plasmid with an origin of replication).

"Expression cassette" as used herein means a nucleic acid sequence capable of directing expression of a particular nucleotide sequence in an appropriate host cell, which may include a promoter operably linked to the nucleotide sequence of interest that may be operably linked to termination signals. The coding region usually codes for a functional RNA of interest, for example an siRNA. The expression cassette including the nucleotide sequence of interest may be chimeric. The expression cassette may also be one that is naturally occurring but has been obtained in a recombinant form useful for heterologous expression. The expression of the nucleotide sequence in the expression cassette may be under the control of a constitutive promoter or of a regulatable promoter that initiates transcription only when the host cell is exposed to some particular stimulus. In the case of a multicellular organism, the promoter can also be specific to a particular tissue or organ or stage of development.

Such expression cassettes can include a transcriptional initiation region linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

"Coding sequence" refers to a DNA or RNA sequence that codes for a specific amino acid sequence. It may constitute an "uninterrupted coding sequence," i.e., lacking an intron, such as in a cDNA, or it may include one or more introns bounded by appropriate splice junctions. An "intron" is a sequence of RNA that is contained in the primary transcript but is removed through cleavage and re-ligation of the RNA within the cell to create the mature mRNA that can be translated into a protein.

The term "open reading frame" (ORF) refers to the sequence between translation initiation and termination codons of a coding sequence. The terms "initiation codon" and "termination codon" refer to a unit of three adjacent nucleotides (a 'codon') in a coding sequence that specifies initiation and chain termination, respectively, of protein synthesis (mRNA translation).

"Functional RNA" refers to sense RNA, antisense RNA, ribozyme RNA, siRNA, or other RNA that may not be translated but yet has an effect on at least one cellular process.

The term "RNA transcript" or "transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell.

"cDNA" refers to a single- or a double-stranded DNA that is complementary to and derived from mRNA.

"Regulatory sequences" are nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted herein, the term "suitable regulatory sequences" is not limited to promoters. However, some suitable regulatory sequences useful in the present invention will include, but are not limited to constitutive promoters, tissue-specific promoters, development-specific promoters, regulatable promoters and viral promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency.

"3' non-coding sequence" refers to nucleotide sequences located 3' (downstream) to a coding sequence and may include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

The term "mature" protein refers to a post-translationally processed polypeptide without its signal peptide. "Precursor" protein refers to the primary product of translation of an mRNA. "Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide.

"Promoter" refers to a nucleotide sequence, usually upstream (5') to its coding sequence, which directs and/or controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions. Examples of promoters that may be used in the present invention include the mouse U6 RNA promoters, synthetic human HI RNA promoters, SV40, CMV, RSV, RNA polymerase II and RNA polymerase III promoters.

The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Operably-linked" refers to the association of nucleic acid sequences on single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene, heterologous gene or nucleic acid segment, or a transgene in cells. For example, in the case of siRNA constructs, expression may refer to the transcription of the siRNA only. In addition, expression refers to the transcription and stable accumulation of sense (mRNA) or functional RNA. Expression may also refer to the production of protein.

"Altered levels" refers to the level of expression in transgenic cells or organisms that differs from that of normal or untransformed cells or organisms.

"Overexpression" refers to the level of expression in transgenic cells or organisms that exceeds levels of expression in normal or untransformed cells or organisms.

"Antisense inhibition" refers to the production of antisense RNA transcripts capable of suppressing the expression of protein from an endogenous gene or a transgene.

"Transcription stop fragment" refers to nucleotide sequences that contain one or more regulatory signals, such as polyadenylation signal sequences, capable of terminating transcription. Examples include the 3' non-regulatory regions of genes encoding nopaline synthase and the small subunit of ribulose bisphosphate carboxylase.

"Translation stop fragment" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

The terms "cis-acting sequence" and "cis-acting element" refer to DNA or RNA sequences whose functions require them to be on the same molecule. An example of a cis-acting sequence on the replicon is the viral replication origin.

The terms "trans-acting sequence" and "trans-acting element" refer to DNA or RNA sequences whose function does not require them to be on the same molecule.

"Chromosomally-integrated" refers to the integration of a foreign gene or nucleic acid construct into the host DNA by covalent bonds. Where genes are not "chromosomally integrated" they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Thus, the determination of percent identity between any two sequences can be accomplished using a mathematical algorithm.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When utilizing BLAST, Gapped BLAST, PSI-BLAST, the default parameters of the respective programs (e.g. BLASTN for nucleotide sequences) can be used. The BLASTN program (for nucleotide sequences) uses as defaults a wordlength (W) of 11, an expectation (E) of 10, a cutoff of 100, M=5, N=−4, and a comparison of both strands. Alignment may also be performed manually by inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide matches and an identical percent sequence identity when compared to the corresponding alignment generated by the preferred program.

(c) As used herein, "sequence identity" or "identity" in the context of two nucleic acid sequences makes reference to a specified percentage of nucleotides in the two sequences that are the same when aligned for maximum correspondence over a specified comparison window, as measured by sequence comparison algorithms or by visual inspection.

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e) The term "substantial identity" of polynucleotide sequences means that a polynucleotide comprises a sequence that has at least 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters.

Another indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted herein, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The Tm is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the Tm can be approximated from the equation: Tm 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. Tm is reduced by about 1° C. for each 1% of mismatching; thus, Tm, hybridization, and/or wash conditions can be adjusted to hybridize to sequences of the desired identity. For example, if sequences with >90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. Generally, highly stringent hybridization and wash conditions are selected to be about 5° C. lower than the thermal melting point (Tm) for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook and Russell 2001, for a description of SSC buffer). Often, a high stringency wash is preceded by a low stringency wash to remove background probe signal.

For short nucleic acid sequences (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. Stringent conditions may also be achieved with the addition of destabilizing agents such as formamide. In general, a signal to noise ratio of 2× (or higher) than that observed for an unrelated probe in the particular hybridization assay indicates detection of a specific hybridization. Very stringent conditions are selected to be equal to the Tm for a particular nucleic acid molecule.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, IM NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

The term "transformation" refers to the transfer of a nucleic acid fragment into the genome of a host cell, resulting in genetically stable inheritance. A "host cell" is a cell that has been transformed, or is capable of transformation, by an exogenous nucleic acid molecule. Host cells containing the transformed nucleic acid fragments are referred to as "transgenic" cells.

"Transformed," "transduced," "transgenic" and "recombinant" refer to a host cell into which a heterologous nucleic acid molecule has been introduced. As used herein the term "transfection" refers to the delivery of DNA into eukaryotic (e.g., mammalian) cells. The term "transformation" is used herein to refer to delivery of DNA into prokaryotic (e.g., E. coli) cells. The term "transduction" is used herein to refer to infecting cells with viral particles. The nucleic acid molecule can be stably integrated into the genome generally known in the art. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

"Genetically altered cells" denotes cells which have been modified by the introduction of recombinant or heterologous nucleic acids (e.g., one or more DNA constructs or their RNA counterparts) and further includes the progeny of such cells which retain part or all of such genetic modification.

As used herein, the term "derived" or "directed to" with respect to a nucleotide molecule means that the molecule has complementary sequence identity to a particular molecule of interest.

The siRNAs of the present invention can be generated by any method known to the art, for example, by in vitro transcription, recombinantly, or by synthetic means. In one example, the siRNAs can be generated in vitro by using a recombinant enzyme, such as T7 RNA polymerase, and DNA oligonucleotide templates.

Nucleic Acid Molecules of the Invention

The terms "isolated and/or purified" refer to in vitro isolation of a nucleic acid, e.g., a DNA or RNA molecule from its natural cellular environment, and from association with other components of the cell, such as nucleic acid or polypeptide, so that it can be sequenced, replicated, and/or expressed. The RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell, e.g., in a vector or plasmid.

In addition to a DNA sequence encoding a siRNA, the nucleic acid molecules of the invention include double-stranded interfering RNA molecules, which are also useful to inhibit expression of a target gene.

As used herein, the term "recombinant nucleic acid", e.g., "recombinant DNA sequence or segment" refers to a nucleic acid, e.g., to DNA, that has been derived or isolated from any appropriate cellular source, that may be subsequently chemically altered in vitro, so that its sequence is not naturally occurring, or corresponds to naturally occurring sequences that are not positioned as they would be positioned in a genome which has not been transformed with exogenous DNA. An example of preselected DNA "derived" from a source would be a DNA sequence that is identified as a useful fragment within a given organism, and which is then chemically synthesized in essentially pure form. An example of such DNA "isolated" from a source would be a useful DNA sequence that is excised or removed from a source by chemical means, e.g., by the use of restriction endonucleases, so that it can be further manipulated, e.g., amplified, for use in the invention, by the methodology of genetic engineering. "Recombinant DNA" includes completely synthetic DNA sequences, semi-synthetic DNA sequences, DNA sequences isolated from biological sources, and DNA sequences derived from RNA, as well as mixtures thereof.

Expression Cassettes of the Invention

To prepare expression cassettes, the recombinant DNA sequence or segment may be circular or linear, double-stranded or single-stranded. Generally, the DNA sequence or segment is in the form of chimeric DNA, such as plasmid DNA or a vector that can also contain coding regions flanked by control sequences that promote the expression of the recombinant DNA present in the resultant transformed cell.

A "chimeric" vector or expression cassette, as used herein, means a vector or cassette including nucleic acid sequences from at least two different species, or has a nucleic acid sequence from the same species that is linked or associated in a manner that does not occur in the "native" or wild type of the species.

Aside from recombinant DNA sequences that serve as transcription units for an RNA transcript, or portions thereof, a portion of the recombinant DNA may be untranscribed, serving a regulatory or a structural function. For example, the recombinant DNA may have a promoter that is active in mammalian cells.

Other elements functional in the host cells, such as introns, enhancers, polyadenylation sequences and the like, may also be a part of the recombinant DNA. Such elements may or may not be necessary for the function of the DNA, but may provide improved expression of the DNA by affecting transcription, stability of the siRNA, or the like. Such elements may be included in the DNA as desired to obtain the optimal performance of the siRNA in the cell.

Control sequences are DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

Operably linked nucleic acids are nucleic acids placed in a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, operably linked DNA sequences are DNA sequences that are linked are contiguous. However, enhancers do not have to be contiguous. Linking is accomplished by ligation at convenient restriction sites. If such sites do not exist, the synthetic oligonucleotide adaptors or linkers are used in accord with conventional practice.

The recombinant DNA to be introduced into the cells may contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. For example, reporter genes include the chloramphenicol acetyl transferase gene (cat) from Tn9 of *E. coli* and the luciferase gene from firefly *Photinus pyralis*. Expression of the reporter gene is assayed at a suitable time after the DNA has been introduced into the recipient cells.

The general methods for constructing recombinant DNA that can transfect target cells are well known to those skilled in the art, and the same compositions and methods of construction may be utilized to produce the DNA useful herein.

The recombinant DNA can be readily introduced into the host cells, e.g., mammalian, bacterial, yeast or insect cells by transfection with an expression vector composed of DNA encoding the siRNA by any procedure useful for the introduction into a particular cell, e.g., physical or biological methods, to yield a cell having the recombinant DNA stably integrated into its genome or existing as a episomal element, so that the DNA molecules, or sequences of the present invention are expressed by the host cell. Preferably, the DNA is introduced into host cells via a vector. The host cell is preferably of eukaryotic origin, e.g., plant, mammalian, insect, yeast or fungal sources, but host cells of non-eukaryotic origin may also be employed.

Physical methods to introduce a preselected DNA into a host cell include calcium phosphate precipitation, lipofection, particle bombardment, microinjection, electroporation, and the like. Biological methods to introduce the DNA of interest into a host cell include the use of DNA and RNA viral vectors. For mammalian gene therapy, as described herein below, it is desirable to use an efficient means of inserting a copy gene into the host genome. Viral vectors, and especially retroviral vectors, have become the most widely used method for inserting genes into mammalian, e.g., human cells. Other viral vectors can be derived from poxviruses, herpes simplex virus I, adenoviruses and adeno-associated viruses, and the like. See, for example, U.S. Pat. Nos. 5,350,674 and 5,585,362.

As discussed herein, a "transfected" "or "transduced" host cell or cell line is one in which the genome has been altered or augmented by the presence of at least one heterologous or recombinant nucleic acid sequence. The host cells of the present invention are typically produced by transfection with a DNA sequence in a plasmid expression vector, a viral expression vector, or as an isolated linear DNA sequence. The transfected DNA can become a chromosomally integrated recombinant DNA sequence, which is composed of sequence encoding the siRNA.

To confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

To detect and quantitate RNA produced from introduced recombinant DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the recombinant DNA segment in question, they do not provide information as to whether the preselected DNA segment is being expressed. Expression may be evaluated by specifically identifying the peptide products of the introduced recombinant DNA sequences or evaluating the phenotypic changes brought about by the expression of the introduced recombinant DNA segment in the host cell.

The instant invention provides a cell expression system for expressing exogenous nucleic acid material in a mammalian recipient. The expression system, also referred to as a "genetically modified cell," comprises a cell and an expression vector for expressing the exogenous nucleic acid material. The genetically modified cells are suitable for administration to a mammalian recipient, where they replace the endogenous cells of the recipient. Thus, the preferred genetically modified cells are non-immortalized and are non-tumorigenic.

According to one embodiment, the cells are transfected or otherwise genetically modified ex vivo. The cells are isolated from a mammal (preferably a human), nucleic acid introduced (i.e., transduced or transfected in vitro) with a vector for expressing a heterologous (e.g., recombinant) gene encoding the therapeutic agent, and then administered to a mammalian recipient for delivery of the therapeutic agent in situ. The mammalian recipient may be a human and the cells to be modified are autologous cells, i.e., the cells are isolated from the mammalian recipient.

According to another embodiment, the cells are transfected or transduced or otherwise genetically modified in vivo. The cells from the mammalian recipient are transduced or transfected in vivo with a vector containing exogenous nucleic acid material for expressing a heterologous (e.g., recombinant) gene encoding a therapeutic agent and the therapeutic agent is delivered in situ.

As used herein, "exogenous nucleic acid material" refers to a nucleic acid or an oligonucleotide, either natural or synthetic, which is not naturally found in the cells; or if it is naturally found in the cells, is modified from its original or native form. Thus, "exogenous nucleic acid material" includes, for example, a non-naturally occurring nucleic acid that can be transcribed into an anti-sense RNA, a siRNA, as well as a "heterologous gene" (i.e., a gene encoding a protein that is not expressed or is expressed at biologically insignificant levels in a naturally-occurring cell of the same type). To illustrate, a synthetic or natural gene encoding human erythropoietin (EPO) would be considered "exogenous nucleic acid material" with respect to human peritoneal mesothelial cells since the latter cells do not naturally express EPO. Still another example of "exogenous nucleic acid material" is the introduction of only part of a gene to create a recombinant gene, such as combining an regulatable promoter with an endogenous coding sequence via homologous recombination.

The condition amenable to gene inhibition therapy may be a prophylactic process, i.e., a process for preventing disease or an undesired medical condition. Thus, the instant invention embraces a system for delivering siRNA that has a prophylactic function (i.e., a prophylactic agent) to the mammalian recipient.

Methods for Introducing the Expression Cassettes of the Invention into Cells

The inhibitory nucleic acid material (e.g., an expression cassette encoding siRNA directed to a gene of interest) can be introduced into the cell ex vivo or in vivo by genetic transfer methods, such as transfection or transduction, to provide a genetically modified cell. Various expression vectors (i.e., vehicles for facilitating delivery of exogenous nucleic acid into a target cell) are known to one of ordinary skill in the art.

As used herein, "transfection of cells" refers to the acquisition by a cell of new nucleic acid material by incorporation of added DNA. Thus, transfection refers to the insertion of nucleic acid into a cell using physical or chemical methods. Several transfection techniques are known to those of ordinary skill in the art including calcium phosphate DNA co-precipitation, DEAE-dextran, electroporation, cationic liposome-mediated transfection, tungsten particle-facilitated microparticle bombardment, and strontium phosphate DNA co-precipitation.

In contrast, "transduction of cells" refers to the process of transferring nucleic acid into a cell using a DNA or RNA virus. A RNA virus (i.e., a retrovirus) for transferring a nucleic acid into a cell is referred to herein as a transducing chimeric retrovirus. Exogenous nucleic acid material contained within the retrovirus is incorporated into the genome of the transduced cell. A cell that has been transduced with a chimeric DNA virus (e.g., an adenovirus carrying a cDNA encoding a therapeutic agent), will not have the exogenous nucleic acid material incorporated into its genome but will be capable of expressing the exogenous nucleic acid material that is retained extrachromosomally within the cell.

The exogenous nucleic acid material can include the nucleic acid encoding the siRNA together with a promoter to control transcription. The promoter characteristically has a specific nucleotide sequence necessary to initiate transcription. The exogenous nucleic acid material may further include additional sequences (i.e., enhancers) required to obtain the desired gene transcription activity. For the purpose of this discussion an "enhancer" is simply any non-translated DNA sequence that works with the coding sequence (in cis) to change the basal transcription level dictated by the promoter. The exogenous nucleic acid material may be introduced into the cell genome immediately downstream from the promoter so that the promoter and coding sequence are operatively linked so as to permit transcription of the coding sequence. An expression vector can include an exogenous promoter element to control transcription of the inserted exogenous gene. Such exogenous promoters include both constitutive and regulatable promoters.

Naturally-occurring constitutive promoters control the expression of essential cell functions. As a result, a nucleic acid sequence under the control of a constitutive promoter is expressed under all conditions of cell growth. Constitutive promoters include the promoters for the following genes which encode certain constitutive or "housekeeping" functions: hypoxanthine phosphoribosyl transferase (HPRT), dihydrofolate reductase (DHFR), adenosine deaminase, phosphoglycerol kinase (PGK), pyruvate kinase, phosphoglycerol mutase, the beta-actin promoter, and other constitutive promoters known to those of skill in the art. In addition, many viral promoters function constitutively in eukaryotic cells. These include: the early and late promoters of SV40; the long terminal repeats (LTRs) of Moloney Leukemia Virus and other retroviruses; and the thymidine kinase promoter of Herpes Simplex Virus, among many others.

Nucleic acid sequences that are under the control of regulatable promoters are expressed only or to a greater or lesser degree in the presence of an inducing or repressing agent, (e.g., transcription under control of the metallothionein promoter is greatly increased in presence of certain metal ions). Regulatable promoters include responsive elements (REs) that stimulate transcription when their inducing factors are bound. For example, there are REs for serum factors, steroid hormones, retinoic acid, cyclic AMP, and tetracycline and doxycycline. Promoters containing a particular RE can be chosen in order to obtain an regulatable response and in some cases, the RE itself may be attached to a different promoter, thereby conferring regulatability to the encoded nucleic acid sequence. Thus, by selecting the appropriate promoter (constitutive versus regulatable; strong versus weak), it is possible to control both the existence and level of expression of a nucleic acid sequence in the genetically modified cell. If the nucleic acid sequence is under the control of an regulatable promoter, delivery of the therapeutic agent in situ is triggered by exposing the genetically modified cell in situ to conditions for permitting transcription of the nucleic acid sequence, e.g., by intraperitoneal injection of specific inducers of the regulatable promoters which control transcription of the agent. For example, in situ expression of a nucleic acid sequence under the control of the metallothionein promoter in genetically modified cells is enhanced by contacting the genetically modified cells with a solution containing the appropriate (i.e., inducing) metal ions in situ.

Accordingly, the amount of siRNA generated in situ is regulated by controlling such factors as the nature of the promoter used to direct transcription of the nucleic acid sequence, (i.e., whether the promoter is constitutive or regulatable, strong or weak) and the number of copies of the exogenous nucleic acid sequence encoding a siRNA sequence that are in the cell.

In addition to at least one promoter and at least one heterologous nucleic acid sequence encoding the siRNA, the expression vector may include a selection gene, for example, a neomycin resistance gene, for facilitating selection of cells that have been transfected or transduced with the expression vector.

Cells can also be transfected with two or more expression vectors, at least one vector containing the nucleic acid sequence(s) encoding the siRNA(s), the other vector containing a selection gene. The selection of a suitable promoter, enhancer, selection gene, and/or signal sequence is deemed to be within the scope of one of ordinary skill in the art without undue experimentation.

The following discussion is directed to various utilities of the instant invention. For example, the instant invention has utility as an expression system suitable for silencing the expression of gene(s) of interest.

The instant invention also provides methods for genetically modifying cells of a mammalian recipient in vivo. According to one embodiment, the method comprises introducing an expression vector for expressing a siRNA sequence in cells of the mammalian recipient in situ by, for example, injecting the vector into the recipient.

Delivery Vehicles for the Expression Cassettes of the Invention

Delivery of compounds into tissues and across the blood-brain barrier can be limited by the size and biochemical properties of the compounds. Currently, efficient delivery of compounds into cells in vivo can be achieved only when the molecules are small (usually less than 600 Daltons). Gene transfer for the correction of inborn errors of metabolism and neurodegenerative diseases of the central nervous system (CNS), and for the treatment of cancer has been accomplished with recombinant adenoviral vectors.

The selection and optimization of a particular expression vector for expressing a specific siRNA in a cell can be accomplished by obtaining the nucleic acid sequence of the siRNA, possibly with one or more appropriate control regions (e.g., promoter, insertion sequence); preparing a vector construct comprising the vector into which is inserted the nucleic acid sequence encoding the siRNA; transfecting or transducing cultured cells in vitro with the vector construct; and determining whether the siRNA is present in the cultured cells.

Vectors for cell gene therapy include viruses, such as replication-deficient viruses (described in detail below). Exemplary viral vectors are derived from Harvey Sarcoma virus, ROUS Sarcoma virus, (MPSV), Moloney murine leukemia virus and DNA viruses (e.g., adenovirus).

Replication-deficient retroviruses are capable of directing synthesis of all virion proteins, but are incapable of making infectious particles. Accordingly, these genetically altered retroviral expression vectors have general utility for high-efficiency transduction of nucleic acid sequences in cultured cells, and specific utility for use in the method of the present invention. Such retroviruses further have utility for the efficient transduction of nucleic acid sequences into cells in vivo. Retroviruses have been used extensively for transferring nucleic acid material into cells. Protocols for producing replication-deficient retroviruses (including the steps of incorporation of exogenous nucleic acid material into a plasmid, transfection of a packaging cell line with plasmid, production of recombinant retroviruses by the packaging cell line, collection of viral particles from tissue culture media, and infection of the target cells with the viral particles) are well known in the art.

An advantage of using retroviruses for gene therapy is that the viruses insert the nucleic acid sequence encoding the siRNA into the host cell genome, thereby permitting the nucleic acid sequence encoding the siRNA to be passed on to the progeny of the cell when it divides. Promoter sequences in the LTR region have can enhance expression of an inserted coding sequence in a variety of cell types. Some disadvantages of using a retrovirus expression vector are (1) insertional mutagenesis, i.e., the insertion of the nucleic acid sequence encoding the siRNA into an undesirable position in the target cell genome which, for example, leads to unregulated cell growth and (2) the need for target cell proliferation in order for the nucleic acid sequence encoding the siRNA carried by the vector to be integrated into the target genome.

Another viral candidate useful as an expression vector for transformation of cells is the adenovirus, a double-stranded DNA virus. The adenovirus is infective in a wide range of cell types, including, for example, muscle and endothelial cells.

Adenoviruses (Ad) are double-stranded linear DNA viruses with a 36 kb genome. Several features of adenovirus have made them useful as transgene delivery vehicles for therapeutic applications, such as facilitating in vivo gene delivery. Recombinant adenovirus vectors have been shown to be capable of efficient in situ gene transfer to parenchymal cells of various organs, including the lung, brain, pancreas, gallbladder, and liver. This has allowed the use of these vectors in methods for treating inherited genetic diseases, such as cystic fibrosis, where vectors may be delivered to a target organ. In addition, the ability of the adenovirus vector to accomplish in situ tumor transduction has allowed the development of a variety of anticancer gene therapy methods for non-disseminated disease. In these methods, vector containment favors tumor cell-specific transduction.

Like the retrovirus, the adenovirus genome is adaptable for use as an expression vector for gene therapy, i.e., by removing the genetic information that controls production of the virus itself. Because the adenovirus functions in an extrachromosomal fashion, the recombinant adenovirus does not have the theoretical problem of insertional mutagenesis.

Several approaches traditionally have been used to generate the recombinant adenoviruses. One approach involves direct ligation of restriction endonuclease fragments containing a nucleic acid sequence of interest to portions of the adenoviral genome. Alternatively, the nucleic acid sequence of interest may be inserted into a defective adenovirus by homologous recombination results. The desired recombinants are identified by screening individual plaques generated in a lawn of complementation cells.

Most adenovirus vectors are based on the adenovirus type 5 (Ad5) backbone in which an expression cassette containing the nucleic acid sequence of interest has been introduced in place of the early region 1 (E1) or early region 3 (E3). Viruses in which E1 has been deleted are defective for replication and are propagated in human complementation cells (e.g., 293 or 911 cells), which supply the missing gene E1 and pIX in trans.

In one embodiment of the present invention, one will desire to generate siRNA in a brain cell or brain tissue. A suitable vector for this application is an FIV vector or an AAV vector. For example, one may use AAV5. Also, one may apply poliovirus or HSV vectors.

Application of siRNA is generally accomplished by transfection of synthetic siRNAs, in vitro synthesized RNAs, or plasmids expressing shRNAs or miRNAs. More recently, viruses have been employed for in vitro studies and to generate transgenic mouse knock-downs of targeted genes. Recombinant adenovirus, adeno-associated virus (AAV) and feline immunodeficiency virus (FIV) can be used to deliver genes in vitro and in vivo. Each has its own advantages and disadvantages. Adenoviruses are double stranded DNA viruses with large genomes (36 kb) and have been engineered by my laboratory and others to accommodate expression cassettes in distinct regions.

Adeno-associated viruses have encapsidated genomes, similar to Ad, but are smaller in size and packaging capacity (~30 nm vs. ~100 nm; packaging limit of ~4.5 kb). AAV contain single stranded DNA genomes of the + or the − strand. Eight serotypes of AAV (1-8) have been studied extensively, three of which have been evaluated in the brain. An important consideration for the present application is that AAV5 transduces striatal and cortical neurons, and is not associated with any known pathologies.

Adeno associated virus (AAV) is a small nonpathogenic virus of the parvoviridae family. AAV is distinct from the other members of this family by its dependence upon a helper virus for replication. In the absence of a helper virus, AAV may integrate in a locus specific manner into the q-arm of chromosome 19. The approximately 5 kb genome of AAV consists of one segment of single stranded DNA of either plus or minus polarity. The ends of the genome are short inverted terminal repeats which can fold into hairpin structures and serve as the origin of viral DNA replication. Physically, the parvovirus virion is non-enveloped and its icosohedral capsid is approximately 20 nm in diameter.

Further provided by this invention are chimeric viruses where AAV can be combined with herpes virus, herpes virus amplicons, baculovirus or other viruses to achieve a desired tropism associated with another virus. For example, the AAV4 ITRs could be inserted in the herpes virus and cells could be infected. Post-infection, the ITRs of AAV4 could be acted on by AAV4 rep provided in the system or in a separate vehicle to rescue AAV4 from the genome. Therefore, the cellular tropism of the herpes simplex virus can be combined with AAV4 rep mediated targeted integration. Other viruses that could be utilized to construct chimeric viruses include lentivirus, retrovirus, pseudotyped retroviral vectors, and adenoviral vectors.

Also provided by this invention are variant AAV vectors. For example, the sequence of a native AAV, such as AAV5, can be modified at individual nucleotides. The present invention includes native and mutant AAV vectors. The present invention further includes all AAV serotypes.

FIV is an enveloped virus with a strong safety profile in humans; individuals bitten or scratched by FIV-infected cats do not seroconvert and have not been reported to show any signs of disease. Like AAV, FIV provides lasting transgene expression in mouse and nonhuman primate neurons, and transduction can be directed to different cell types by pseudotyping, the process of exchanging the virus's native envelope for an envelope from another virus.

Thus, as will be apparent to one of ordinary skill in the art, a variety of suitable viral expression vectors are available for transferring exogenous nucleic acid material into cells. The selection of an appropriate expression vector to express a therapeutic agent for a particular condition amenable to gene silencing therapy and the optimization of the conditions for insertion of the selected expression vector into the cell, are within the scope of one of ordinary skill in the art without the need for undue experimentation.

In another embodiment, the expression vector is in the form of a plasmid, which is transferred into the target cells by one of a variety of methods: physical (e.g., microinjection, electroporation, scrape loading, microparticle bombardment) or by cellular uptake as a chemical complex (e.g., calcium or strontium co-precipitation, complexation with lipid, complexation with ligand). Several commercial products are available for cationic liposome complexation including Lipofectin™ (Gibco-BRL, Gaithersburg, Md.) and Transfectam™ (Promega®, Madison, Wis.). However, the efficiency of transfection by these methods is highly dependent on the nature of the target cell and accordingly, the conditions for optimal transfection of nucleic acids into cells using the herein-mentioned procedures must be optimized. Such optimization is within the scope of one of ordinary skill in the art without the need for undue experimentation.

Adeno Associated Virus (AAV)

Adeno associated virus (AAV) is a small nonpathogenic virus of the parvoviridae family. AAV is distinct from the other members of this family by its dependence upon a helper virus for replication. In the absence of a helper virus, AAV may integrate in a locus specific manner into the q arm of chromosome 19. The approximately 5 kb genome of AAV consists of one segment of single stranded DNA of either plus or minus polarity. The ends of the genome are short inverted terminal repeats which can fold into hairpin structures and serve as the origin of viral DNA replication. Physically, the parvovirus virion is non-enveloped and its icosohedral capsid is approximately 20 nm in diameter.

To date, numerous serologically distinct AAVs have been identified, and more than a dozen have been isolated from humans or primates. The genome of AAV2 is 4680 nucleotides in length and contains two open reading frames (ORFs). The left ORF encodes the non-structural Rep proteins, Rep 40, Rep 52, Rep 68 and Rep 78, which are involved in regulation of replication and transcription in addition to the production of single-stranded progeny genomes. Furthermore, two of the Rep proteins have been associated with the preferential integration of AAV genomes into a region of the q arm of human chromosome 19. Rep68/78 has also been shown to possess NTP binding activity as well as DNA and RNA helicase activities. The Rep proteins possess a nuclear localization signal as well as several potential phosphorylation sites. Mutation of one of these kinase sites resulted in a loss of replication activity.

The ends of the genome are short inverted terminal repeats (ITR) which have the potential to fold into T-shaped hairpin structures that serve as the origin of viral DNA replication. Within the ITR region two elements have been described which are central to the function of the ITR, a GAGC repeat motif and the terminal resolution site (trs). The repeat motif has been shown to bind Rep when the ITR is in either a linear or hairpin conformation. This binding serves to position Rep68/78 for cleavage at the trs which occurs in a site- and strand-specific manner. In addition to their role in replication, these two elements appear to be central to viral integration. Contained within the chromosome 19 integration locus is a Rep binding site with an adjacent trs. These elements have been shown to be functional and necessary for locus specific integration.

The AAV virion is a non-enveloped, icosohedral particle approximately 25 nm in diameter, consisting of three related proteins referred to as VP1, VP2 and VP3. The right ORF encodes the capsid proteins VP1, VP2, and VP3. These proteins are found in a ratio of 1:1:10 respectively and are all derived from the right-hand ORF. The capsid proteins differ from each other by the use of alternative splicing and an unusual start codon. Deletion analysis has shown that removal or alteration of VP1 which is translated from an alternatively spliced message results in a reduced yield of infections particles. Mutations within the VP3 coding region result in the failure to produce any single-stranded progeny DNA or infectious particles. An AAV particle is a viral particle comprising an AAV capsid protein. An AAV capsid polypeptide can encode the entire VP1, VP2 and VP3 polypeptide. The particle can be a particle comprising AAV2 and other AAV capsid proteins (i.e., a chimeric protein, such as AAV1 and AAV2). Variations in the amino acid sequence of the AAV2 capsid protein are contemplated herein, as long as the resulting viral particle comprises the AAV2 capsid remains antigenically or immunologically distinct from AAV1, as can be routinely determined by standard methods. Specifically, for example, ELISA and Western blots can be used to determine whether a viral particle is antigenically or immunologically distinct from AAV1. Furthermore, the AAV2 viral particle preferably retains tissue tropism distinct from AAV1.

An AAV2 particle is a viral particle comprising an AAV2 capsid protein. An AAV2 capsid polypeptide encoding the entire VP1, VP2, and VP3 polypeptide can overall have at least about 63% homology (or identity) to the polypeptide having the amino acid sequence encoded by nucleotides set forth in NC_001401 (nucleotide sequence encoding AAV2 capsid protein). The capsid protein can have about 70% homology, about 75% homology, 80% homology, 85% homology, 90% homology, 95% homology, 98% homology, 99% homology, or even 100% homology to the protein encoded by the nucleotide sequence set forth in NC_001401. The capsid protein can have about 70% identity, about 75% identity, 80% identity, 85% identity, 90% identity, 95% identity, 98% identity, 99% identity, or even 100% identity to the protein encoded by the nucleotide sequence set forth in NC_001401. The particle can be a particle comprising another AAV and AAV2 capsid protein, i.e., a chimeric protein. Variations in the amino acid sequence of the AAV2 capsid protein are contemplated herein, as long as the resulting viral particle comprising the AAV2 capsid remains antigenically or immunologically distinct from AAV4, as can be routinely determined by standard methods. Specifically, for example, ELISA and Western blots can be used to determine whether a viral particle is antigenically or immunologically distinct from AAV1. Furthermore, the AAV2 viral particle preferably retains tissue tropism distinction from AAV1, such as that exemplified in the examples herein, though an AAV2 chimeric particle comprising at least one AAV2 coat protein may have a different tissue tropism from that of an AAV2 particle consisting only of AAV2 coat proteins.

In certain embodiments, the invention further provides an AAV2 particle containing, i.e., encapsidating, a vector comprising a pair of AAV2 inverted terminal repeats. The nucleotide sequence of AAV2 ITRs is known in the art. Furthermore, the particle can be a particle comprising both AAV1 and AAV2 capsid protein, i.e., a chimeric protein. Moreover, the particle can be a particle encapsidating a vector comprising a pair of AAV inverted terminal repeats from other AAVs (e.g., AAV1-AAV9 and AAVrh10). The vector encapsidated in the particle can further comprise an exogenous nucleic acid inserted between the inverted terminal repeats.

The following features of AAV have made it an attractive vector for gene transfer. AAV vectors have been shown in vitro to stably integrate into the cellular genome; possess a broad host range; transduce both dividing and non-dividing cells in vitro and in vivo and maintain high levels of expression of the transduced genes. Viral particles are heat stable, resistant to solvents, detergents, changes in pH, temperature, and can be concentrated on CsCl gradients or by other means. The present invention provides methods of administering AAV particles, recombinant AAV vectors, and recombinant AAV virions. For example, an AAV2 particle is a viral particle comprising an AAV2 capsid protein, or an AAV1 particle is a viral particle comprising an AAV1 capsid protein. A recombinant AAV2 vector is a nucleic acid construct that comprises at least one unique nucleic acid of AAV2. A recombinant AAV2 virion is a particle containing a recombinant AAV2 vector. To be considered within the term "AAV2 ITRs" the nucleotide sequence must retain one or both features described herein that distinguish the AAV2 ITR from the AAV1 ITR: (1) three (rather than four as in AAV1) "GAGC" repeats and (2) in the AAV2 ITR Rep binding site the fourth nucleotide in the first two "GAGC" repeats is a C rather than a T.

The promoter to drive expression of the protein or the sequence encoding another agent to be delivered can be any desired promoter, selected by known considerations, such as the level of expression of a nucleic acid functionally linked to the promoter and the cell type in which the vector is to be used. Promoters can be an exogenous or an endogenous promoter. Promoters can include, for example, known strong promoters such as SV40 or the inducible metallothionein promoter, or an AAV promoter, such as an AAV p5 promoter. Additional examples of promoters include promoters derived from actin genes, immunoglobulin genes, cytomegalovirus (CMV), adenovirus, bovine papilloma virus, adenoviral promoters, such as the adenoviral major late promoter, an inducible heat shock promoter, respiratory syncytial virus, Rous sarcomas virus (RSV), etc. Additional examples include regulated promoters.

The AAV vector can further comprise an exogenous (heterologous) nucleic acid functionally linked to the promoter. By "heterologous nucleic acid" is meant that any heterologous or exogenous nucleic acid can be inserted into the vector for transfer into a cell, tissue or organism. The nucleic acid can encode a polypeptide or protein or an antisense RNA, for example. By "functionally linked" is meant such that the promoter can promote expression of the heterologous nucleic acid, as is known in the art, such as appropriate orientation of the promoter relative to the heterologous nucleic acid. Furthermore, the heterologous nucleic acid preferably has all appropriate sequences for expression of the nucleic acid, as known in the art, to functionally encode, i.e., allow the nucleic acid to be expressed. The nucleic acid can include, for example, expression control sequences, such as an enhancer, and necessary information processing sites, such as ribosome binding sites, RNA splice sites, polyadenylation sites, and transcriptional terminator sequences. The nucleic acid can encode more than one gene product, limited only by the size of nucleic acid that can be packaged.

In certain embodiments of the present invention, the heterologous nucleic acid can encode beneficial proteins that replace missing or defective proteins required by the subject into which the vector in transferred, such as Rheb or Rhes.

An AAV1 particle is a viral particle comprising an AAV1 capsid protein. Variations in the amino acid sequence of the AAV1 capsid protein are contemplated herein, as long as the resulting viral particle comprising the AAV1 capsid remains antigenically or immunologically distinct from other AAV capsids, as can be routinely determined by standard methods. Specifically, for example, ELISA and Western blots can be used to determine whether a viral particle is antigenically or immunologically distinct from other AAV serotypes.

The term "polypeptide" as used herein refers to a polymer of amino acids and includes full-length proteins and fragments thereof. Thus, "protein" and "polypeptide" are often used interchangeably herein. Substitutions can be selected by known parameters to be neutral. As will be appreciated by those skilled in the art, the invention also includes those polypeptides having slight variations in amino acid sequences or other properties. Such variations may arise naturally as allelic variations (e.g. due to genetic polymorphism) or may be produced by human intervention (e.g., by mutagenesis of cloned DNA sequences), such as induced point, deletion, insertion and substitution mutants. Minor changes in amino acid sequence are generally preferred, such as conservative amino acid replacements, small internal deletions or insertions, and additions or deletions at the ends of the molecules. These modifications can result in changes in the amino acid sequence, provide silent mutations, modify a restriction site, or provide other specific mutations.

The present method provides a method of delivering a nucleic acid to a cell comprising administering to the cell an AAV particle containing a vector comprising the nucleic acid inserted between a pair of AAV inverted terminal repeats, thereby delivering the nucleic acid to the cell. Administration to the cell can be accomplished by any means, including simply contacting the particle, optionally contained in a desired liquid such as tissue culture medium, or a buffered saline solution, with the cells. The particle can be allowed to remain in contact with the cells for any desired length of time, and typically the particle is administered and allowed to remain indefinitely. For such in vitro methods, the virus can be administered to the cell by standard viral transduction methods, as known in the art and as exemplified herein. Titers of virus to administer can vary, particularly depending upon the cell type, but will be typical of that used for AAV transduction in general. Additionally the titers used to transduce the particular cells in the present examples can be utilized. The cells can include any desired cell in humans as well as other large (non-rodent) mammals, such as primates, horse, sheep, goat, pig, and dog.

More specifically, the present invention provides a method of delivering a nucleic acid to a cell in the brain, particularly medium spiny neurons, comprising the nucleic acid inserted between a pair of AAV inverted terminal repeats, thereby delivering the nucleic acid to the cell.

The present invention further provides a method of delivering a nucleic acid to a cell in a subject comprising administering to the subject an AAV particle comprising the nucleic acid inserted between a pair of AAV inverted terminal repeats, thereby delivering the nucleic acid to a cell in the subject.

Also provided is a method of delivering a nucleic acid to a brain cell, such as a neuron in the striatum or cortex in a subject comprising administering to the subject an AAV particle comprising the nucleic acid inserted between a pair of AAV inverted terminal repeats, thereby delivering the nucleic acid to the neuron or other cell in the subject.

Certain embodiments of the present disclosure provide a cell comprising a viral vector as described herein.

AAV Vectors

In one embodiment, a viral vector of the disclosure is an AAV vector. An "AAV" vector refers to an adeno-associated virus, and may be used to refer to the naturally occurring wild-type virus itself or derivatives thereof. The term covers all subtypes, serotypes and pseudotypes, and both naturally occurring and recombinant forms, except where required otherwise. As used herein, the term "serotype" refers to an AAV which is identified by and distinguished from other AAVs based on capsid protein reactivity with defined antisera, e.g., there are eight known serotypes of primate AAVs, AAV-1 to AAV-9 and AAVrh10. For example, serotype AAV2 is used to refer to an AAV which contains capsid proteins encoded from the cap gene of AAV2 and a genome containing 5' and 3' ITR sequences from the same AAV2 serotype. As used herein, for example, rAAV1 may be used to refer an AAV having both capsid proteins and 5'-3' ITRs from the same serotype or it may refer to an AAV having capsid proteins from one serotype and 5'-3' ITRs from a different AAV serotype, e.g., capsid from AAV serotype 2 and ITRs from AAV serotype 5. For each example illustrated herein the description of the vector design and production describes the serotype of the capsid and 5'-3' ITR sequences. The abbreviation "rAAV" refers to recombinant adeno-associated virus, also referred to as a recombinant AAV vector (or "rAAV vector").

An "AAV virus" or "AAV viral particle" refers to a viral particle composed of at least one AAV capsid protein (preferably by all of the capsid proteins of a wild-type AAV) and an encapsidated polynucleotide. If the particle comprises heterologous polynucleotide (i.e., a polynucleotide other than a wild-type AAV genome such as a transgene to be delivered to a mammalian cell), it is typically referred to as "rAAV".

In one embodiment, the AAV expression vectors are constructed using known techniques to at least provide as operatively linked components in the direction of transcription, control elements including a transcriptional initiation region, the DNA of interest and a transcriptional termination region. The control elements are selected to be functional in a mammalian cell. The resulting construct which contains the operatively linked components is flanked (5' and 3') with functional AAV ITR sequences.

By "adeno-associated virus inverted terminal repeats" or "AAV ITRs" is meant the art-recognized regions found at each end of the AAV genome which function together in cis as origins of DNA replication and as packaging signals for the virus. AAV ITRs, together with the AAV rep coding region, provide for the efficient excision and rescue from, and integration of a nucleotide sequence interposed between two flanking ITRs into a mammalian cell genome.

The nucleotide sequences of AAV ITR regions are known. As used herein, an "AAV ITR" need not have the wild-type nucleotide sequence depicted, but may be altered, e.g., by the insertion, deletion or substitution of nucleotides. Additionally, the AAV ITR may be derived from any of several AAV serotypes, including without limitation, AAV1, AAV2, AAV3, AAV4, AAV5, AAV7, etc. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell.

In one embodiment, AAV ITRs can be derived from any of several AAV serotypes, including without limitation, AAV1, AAV2, AAV3, AAV4, AAV5, AAV7, etc. Furthermore, 5' and 3' ITRs which flank a selected nucleotide sequence in an AAV expression vector need not necessarily be identical or derived from the same AAV serotype or isolate, so long as they function as intended, i.e., to allow for excision and rescue of the sequence of interest from a host cell genome or vector, and to allow integration of the DNA molecule into the recipient cell genome when AAV Rep gene products are present in the cell.

In one embodiment, AAV capsids can be derived from AAV2. Suitable DNA molecules for use in AAV vectors will be less than about 5 kilobases (kb), less than about 4.5 kb, less than about 4 kb, less than about 3.5 kb, less than about 3 kb, less than about 2.5 kb in size and are known in the art.

In one embodiment, the selected nucleotide sequence is operably linked to control elements that direct the transcription or expression thereof in the subject in vivo. Such control elements can comprise control sequences normally associated with the selected gene. Alternatively, heterologous control sequences can be employed. Useful heterologous control sequences generally include those derived from sequences encoding mammalian or viral genes. Examples include, but are not limited to, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, pol II promoters, pol III promoters, synthetic promoters, hybrid promoters, and the like. In addition, sequences derived from nonviral genes, such as the murine metallothionein gene, will also find use herein. Such promoter sequences are commercially available from, e.g., Stratagene (San Diego, Calif.).

In one embodiment, both heterologous promoters and other control elements, such as CNS-specific and inducible promoters, enhancers and the like, will be of particular use. Examples of heterologous promoters include the CMV promoter. Examples of CNS-specific promoters include those isolated from the genes from myelin basic protein (MBP), glial fibrillary acid protein (GFAP), and neuron specific enolase (NSE). Examples of inducible promoters include DNA responsive elements for ecdysone, tetracycline, hypoxia and aufin.

In one embodiment, the AAV expression vector which harbors the DNA molecule of interest bounded by AAV ITRs, can be constructed by directly inserting the selected sequence(s) into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art.

Alternatively, AAV ITRs can be excised from the viral genome or from an AAV vector containing the same and fused 5' and 3' of a selected nucleic acid construct that is present in another vector using standard ligation techniques. For example, ligations can be accomplished in 20 mM Tris-Cl pH 7.5, 10 mM MgCl$_2$, 10 mM DTT, 33 μg/ml BSA, 10 mM-50 mM NaCl, and either 40 uM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 30-100 μg/ml total DNA concentrations (5-100 nM total end concentration). AAV vectors which contain ITRs.

Additionally, chimeric genes can be produced synthetically to include AAV ITR sequences arranged 5' and 3' of one or more selected nucleic acid sequences. Preferred codons for expression of the chimeric gene sequence in mammalian CNS cells can be used. The complete chimeric sequence is assembled from overlapping oligonucleotides prepared by standard methods.

In order to produce rAAV virions, an AAV expression vector is introduced into a suitable host cell using known techniques, such as by transfection. A number of transfection techniques are generally known in the art. See, e.g., Sambrook et al. (1989) Molecular Cloning, a laboratory manual, Cold Spring Harbor Laboratories, New York. Particularly suitable transfection methods include calcium phosphate co-precipitation, direct micro-injection into cultured cells, electroporation, liposome mediated gene transfer, lipid-mediated transduction, and nucleic acid delivery using high-velocity microprojectiles.

In one embodiment, suitable host cells for producing rAAV virions include microorganisms, yeast cells, insect cells, and mammalian cells, that can be, or have been, used as recipients of a heterologous DNA molecule. The term includes the progeny of the original cell which has been transfected. Thus, a "host cell" as used herein generally refers to a cell which has been transfected with an exogenous DNA sequence. Cells from the stable human cell line, 293 (readily available through, e.g., the American Type Culture Collection under Accession Number ATCC CRL1573) can be used in the practice of the present disclosure. Particularly, the human cell line 293 is a human embryonic kidney cell line that has been transformed with adenovirus type-5 DNA fragments, and expresses the adenoviral E1a and E1b genes. The 293 cell line is readily transfected, and provides a particularly convenient platform in which to produce rAAV virions.

By "AAV rep coding region" is meant the art-recognized region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome. Suitable homologues of the AAV rep coding region include the human herpesvirus 6 (HHV-6) rep gene which is also known to mediate AAV-2 DNA replication.

By "AAV cap coding region" is meant the art-recognized region of the AAV genome which encodes the capsid proteins VP1, VP2, and VP3, or functional homologues thereof. These Cap expression products supply the packaging functions which are collectively required for packaging the viral genome.

In one embodiment, AAV helper functions are introduced into the host cell by transfecting the host cell with an AAV helper construct either prior to, or concurrently with, the transfection of the AAV expression vector. AAV helper constructs are thus used to provide at least transient expression of AAV rep and/or cap genes to complement missing AAV functions that are necessary for productive AAV infection. AAV helper constructs lack AAV ITRs and can neither replicate nor package themselves. These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. A number of other vectors have been described which encode Rep and/or Cap expression products. Methods of delivery of viral vectors include injecting the AAV into the subject.

Generally, rAAV virions may be introduced into cells of the CNS using either in vivo or in vitro transduction techniques. If transduced in vitro, the desired recipient cell will be removed from the subject, transduced with rAAV virions and reintroduced into the subject. Alternatively, syngeneic or xenogeneic cells can be used where those cells will not generate an inappropriate immune response in the subject.

Suitable methods for the delivery and introduction of transduced cells into a subject have been described. For example, cells can be transduced in vitro by combining recombinant AAV virions with CNS cells e.g., in appropriate media, and screening for those cells harboring the DNA of interest can be screened using conventional techniques such as Southern blots and/or PCR, or by using selectable markers. Transduced cells can then be formulated into pharmaceutical compositions, described more fully below, and the composition introduced into the subject by various techniques, such as by grafting, intramuscular, intravenous, subcutaneous and intraperitoneal injection.

In one embodiment, pharmaceutical compositions will comprise sufficient genetic material to produce a therapeutically effective amount of the nucleic acid of interest, i.e., an amount sufficient to reduce or ameliorate symptoms of the disease state in question or an amount sufficient to confer the desired benefit. The pharmaceutical compositions will also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, sorbitol, Tween80, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in Remington's Pharmaceutical Sciences (Mack Pub. Co., N.J. 1991).

It should be understood that more than one transgene could be expressed by the delivered viral vector. Alternatively, separate vectors, each expressing one or more different transgenes, can also be delivered to the subject as described herein. Furthermore, it is also intended that the viral vectors delivered by the methods of the present disclosure be combined with other suitable compositions and therapies.

As is apparent to those skilled in the art in view of the teachings of this specification, an effective amount of viral vector which must be added can be empirically determined. Administration can be effected in one dose, continuously or intermittently throughout the course of treatment. Methods of determining the most effective means and dosages of administration are well known to those of skill in the art and will vary with the viral vector, the composition of the therapy, the target cells, and the subject being treated. Single and multiple administrations can be carried out with the dose level and pattern being selected by the treating physician.

In certain embodiments, the rAAV is administered at a dose of about 0.3-2 ml of $1\times10^5$-$1\times10^{16}$ vg/ml. In certain embodiments, the rAAV is administered at a dose of about 1-3 ml of $1\times10^7$-$1\times10^{14}$ vg/ml. In certain embodiments, the rAAV is administered at a dose of about 1-2 ml of $1\times10^8$-$1\times10^{13}$ vg/ml.

Formulations containing the rAAV particles will contain an effective amount of the rAAV particles in a vehicle, the effective amount being readily determined by one skilled in the art. The rAAV particles may typically range from about 1% to about 95% (w/w) of the composition, or even higher or lower if appropriate. The quantity to be administered depends upon factors such as the age, weight and physical condition of the animal or the human subject considered for treatment. Effective dosages can be established by one of ordinary skill in the art through routine trials establishing dose response curves. The subject is treated by administration of the rAAV particles in one or more doses. Multiple doses may be administered as is required to maintain adequate enzyme activity.

Vehicles including water, aqueous saline, artificial CSF, or other known substances can be employed with the subject invention. To prepare a formulation, the purified composition can be isolated, lyophilized and stabilized. The composition may then be adjusted to an appropriate concentration, optionally combined with an anti-inflammatory agent, and packaged for use.

The present invention provides a method of increasing the level of a target protein in a cell by introducing a protein, or nucleic acid molecule encoding a protein described above into a cell in an amount sufficient to increase the level of the target protein in the cell. In certain embodiments, the accumulation of target protein is increased by at least 10%. The accumulation of target protein is increased by at least 10%, 20%, 30%, 40%, 50%, 60%, 70%, 80%, 90% 95%, or 99%.

Furthermore, the AAV vector may be selected/designed according to the desired route of administration, for example, and without limitation, for systemic administration, an AAV vector capable of crossing the blood-brain barrier may be used (e.g., AAV9, or a chimeric AAV vector having AAV9 capsid proteins). The present invention also provides a method of administering AAV to the bloodstream since some serotypes are capable of traversing the blood-brain barrier.

Targeting Peptides

Peptides have been identified that function to target agents, such as viral vectors, to vascular endothelial cells of the central nervous system. The present disclosure describes a method to utilize these novel peptides to redirect, for example, viral capsids to the cell type of interest. In this instance, endothelial cells lining brain blood vessels are targeted by the identified peptides. Vectors harboring capsid proteins modified to include such peptides can be used to provide therapeutic agents to the central nervous system (e.g., the brain).

As used herein, the term "targets" means that the capsid protein of a virus, such as an adeno-associated virus (AAV), preferentially binds to one type of tissue (e.g., brain tissue) over another type of tissue (e.g., liver tissue), and/or binds to a tissue in a certain state (e.g., wildtype or diseased). In certain embodiments, the genetically modified capsid protein may "target" brain vascular epithelia tissue by binding at level of 10% to 1000% higher than a comparable, unmodified capsid protein. For example, an AAV having a genetically-modified capsid protein may bind to brain vascular epithelia tissue at a level 50% to 100% greater than an unmodified AAV virus. In certain embodiments, the nucleic acids encoding the capsid proteins of a virus are modified such that the viral capsids preferentially bind to brain vascular endothelium in a mammal suffering from lysosomal storage disease, or, using different sequences, to wildtype brain vascular endothelium in brain of the same species.

The present invention provides a modified adeno-associated virus (AAV) capsid protein containing a targeting peptide, wherein the targeting peptide is from 3 to 10 amino acids in length and wherein the targeting peptide targets an AAV to brain vascular endothelium. In certain embodiments, the targeting peptide is 3, 4, 5, 6 or 7 amino acids in length. In certain embodiments, the AAV is AAV2, although the tropism is modified so it would follow that such modifications would change the tropism of any AAV.

Certain embodiments of the present disclosure provide a viral vector comprising a modified capsid, wherein the modified capsid comprises at least one amino acid sequence that targets the viral vector to brain vascular endothelium.

In certain embodiments, the viral vector is an adeno associated viral vector (AAV). In certain embodiments, the AAV is AAV2.

In certain embodiments, the targeting peptide targets wildtype brain vascular endothelium. In certain embodiments, the targeting peptide is PXXPS (SEQ ID NO:44), SPXXP (SEQ ID NO:45), TLH (SEQ ID NO:46), or QSXY (SEQ ID NO:47), as expressed in an amino to carboxy orientation or in a carboxy to amino orientation. In certain embodiments, the targeting peptide is PYFPSLS (SEQ ID NO:48), YAPLTPS (SEQ ID NO:49), PLSPSAY (SEQ ID NO:50), DSPAHPS (SEQ ID NO:51), GTPTHPS (SEQ ID NO:52), PDAPSNH (SEQ ID NO:53), TEPHWPS (SEQ ID NO:54), SPPLPPK (SEQ ID NO:55), SPKPPPG (SEQ ID NO:56), NWSPWDP (SEQ ID NO:57), DSPAHPS (SEQ ID NO:58), GWTLHNK (SEQ ID NO:59), KIPPTLH (SEQ ID NO:60), ISQTLHG (SEQ ID NO:61), QSFYILT (SEQ ID NO:62), or TTQSEYG (SEQ ID NO:63), as expressed in an amino to carboxy orientation or in a carboxy to amino orientation. It should be noted that the orientation of the sequence is not important. For example, the peptide may be oriented from the amino-terminal end to carboxy-terminal end of the peptide to be TTQSEYG (SEQ ID NO:63) or may be from the amino-terminal end to carboxy-terminal end of the peptide to be GYESQTT (SEQ ID NO:65).

In certain embodiments, the targeting peptide targets a diseased brain vascular endothelium. In certain embodiments, the targeting peptide targets brain vascular endothelium in a subject that has a lysosomal storage disease. In certain embodiments, the targeting peptide targets a mucopolysaccharide (MPS) VII brain vascular endothelium. In certain embodiments, the targeting peptide is LXSS (SEQ ID NO:66), PFXG (SEQ ID NO:67), or SIXA (SEQ ID NO:68), as expressed in an amino to carboxy orientation or in a carboxy to amino orientation. In certain embodiments, the targeting peptide is MLVSSPA (SEQ ID NO:69), LPSSLQK (SEQ ID NO:70), PPLLKSS (SEQ ID NO:71), PXKLDSS (SEQ ID NO:72), AWTLASS (SEQ ID NO:73), WPFYGTP (SEQ ID NO:74), GTFPFLG (SEQ ID NO:75), GQVPFMG (SEQ ID NO:76), ANFSILA (SEQ ID NO:77), GSIWAPA (SEQ ID NO:78), or SIAASFS (SEQ ID NO:79), as expressed in an amino to carboxy orientation or in a carboxy to amino orientation.

In certain embodiments, targeting peptide targets TPP1 brain vascular endothelium. In certain embodiments, the targeting peptide is GMNAFRA (SEQ ID NO:64), as expressed in an amino to carboxy orientation or in a carboxy to amino orientation.

In certain embodiments, the amino acid sequence that targets brain vascular endothelium comprises at least one of SEQ ID NOs 44-47.

In certain embodiments, the amino acid sequence that targets brain vascular endothelium comprises at least one of SEQ ID NOs 66-68.

In certain embodiments, the amino acid sequence that targets brain vascular endothelium comprises at least one of SEQ ID NOs 48-63.

In certain embodiments, the amino acid sequence that targets brain vascular endothelium comprises at least one of SEQ ID NOs 69-79.

In certain embodiments, the amino acid sequence that targets brain tissue is selected from those listed in Table 1 below:

TABLE 1

Brain targeting PM-AAV

| Name | Sequence | SEQ ID NO. | Targeting |
|---|---|---|---|
| THR | THRPPMWSPVWP | 80 | Transferrin |
| CRT | CRTIGPSVC | 81 | Transferrin |
| BX2 | GHKVKRPKG | 82 | Transferrin |
| BX3 | KDKIKMDKK | 83 | Transferrin |
| BX6 | GHKAKGPRK | 84 | Transferrin |
| BX8 | KWKTPKVRV | 85 | Transferrin |
| AAV-PPS | DSPAHPS | 51 | Wild Type |
| | PYFPSLS | 48 | Wild Type |
| | YAPLTPS | 49 | Wild Type |
| | PLSPSAY | 50 | Wild Type |
| | GTPTHPS | 52 | Wild Type |
| | PDAPSNH | 53 | Wild Type |
| | TEPHWPS | 54 | Wild Type |
| | SPPLPPK | 55 | Wild Type |
| | SPKPPPG | 56 | Wild Type |
| | NWSPWDP | 57 | Wild Type |
| AAV-TLH | GWTLHNK | 59 | Wild Type |
| | KIPPTLH | 60 | Wild Type |
| | ISQTLHG | 61 | Wild Type |
| | QSFYILT | 62 | Wild Type |
| | TTQSEYG | 63 | Wild Type |
| AAV-PFG | WPFYGTP | 74 | MPS VII |
| | GTFPFLG | 75 | MPS VII |
| | GQVPFMG | 76 | MPS VII |
| | PPLLKSS | 71 | MPS VII |
| | MLVSSPA | 69 | MPS VII |
| | AWTLASS | 73 | MPS VII |

TABLE 1-continued

Brain targeting PM-AAV

| Name | Sequence | SEQ ID NO. | Targeting |
|---|---|---|---|
| AAV-LSS | LPSSLQK | 70 | MPS VII |
| | PXKLDSS | 72 | MPS VII |
| | GSIWAPA | 78 | MPS VII |
| | ANFSILA | 77 | MPS VII |
| | SIAASFS | 79 | MPS VII |
| AAV-GMN | GMNAFRA | 64 | CLN2 |

In certain embodiments, the amino acid sequence that targets brain vascular endothelium targets brain vascular endothelium in a subject that has a disease, e.g., a lysosomal storage disease.

In certain embodiments, the amino acid sequence that targets brain vascular endothelium targets brain vascular endothelium in a subject that does not have a lysosomal storage disease.

In certain embodiments, the viral vector comprises a nucleic acid sequence encoding a therapeutic agent. In certain embodiments, the therapeutic agent is β-glucuronidase.

In certain embodiments, the amino acid sequence that targets brain vascular endothelium is at most ten amino acids in length.

In certain embodiments, the amino acid sequence that targets brain vascular endothelium is 3, 4, 5, 6 or 7 amino acids in length.

Certain embodiments of the present disclosure provide a nucleic acid sequence encoding a viral vector as described herein.

Certain embodiments of the present disclosure provide a nucleic acid sequence encoding a modified capsid as described herein. Certain embodiments of the present disclosure provide a modified capsid encoded by a nucleic acid sequence described herein.

Certain embodiments of the present disclosure provide a cell comprising a viral vector as described herein.

Certain embodiments of the present disclosure provide a cell transduced by a viral vector as described herein.

In certain embodiments, the cell is a mammalian cell. In certain embodiments, the cell is a human cell. In certain embodiments, the cell is a non-human cell. In certain embodiments, the cell is in vitro. In certain embodiments, the cell is in vivo. In certain embodiments, the cell is an endothelial cell. In certain embodiments, the cell is a vascular endothelial cell.

Dosages, Formulations and Routes of Administration of the Agents of the Invention The agents of the invention are preferably administered so as to result in a reduction in at least one symptom associated with a disease. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems, which are well known to the art. As used herein, the term "therapeutic siRNA" refers to any siRNA that has a beneficial effect on the recipient. Thus, "therapeutic siRNA" embraces both therapeutic and prophylactic siRNA.

Administration of siRNA may be accomplished through the administration of the nucleic acid molecule encoding the siRNA. Pharmaceutical formulations, dosages and routes of administration for nucleic acids are generally known.

The present invention envisions treating Huntington's disease in a mammal by the administration of an agent, e.g., a nucleic acid composition, an expression vector, or a viral particle of the invention. Administration of the therapeutic agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated.

One or more suitable unit dosage forms having the therapeutic agent(s) of the invention, which, as discussed below, may optionally be formulated for sustained release (for example using microencapsulation, see WO 94/07529, and U.S. Pat. No. 4,962,091 the disclosures of which are incorporated by reference herein), can be administered by a variety of routes including parenteral, including by intravenous and intramuscular routes, as well as by direct injection into the diseased tissue. For example, the therapeutic agent may be directly injected into the brain. Alternatively the therapeutic agent may be introduced intrathecally for brain and spinal cord conditions. In another example, the therapeutic agent may be introduced intramuscularly for viruses that traffic back to affected neurons from muscle, such as AAV, lentivirus and adenovirus. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules, as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions such as phosphate buffered saline solutions pH 7.0-8.0 saline solutions and water.

The invention will now be illustrated by the following non-limiting Example.

EXAMPLE 1

Single Nucleotide Seed Modification Restores In Vivo Tolerability of a Toxic miRNA Sequence in the Mouse Brain Huntington's disease (HD) is a fatal neurodegenerative disease caused by the expression of a polyglutamine-expanded form of huntingtin (HTT). Recent work showed that gene silencing approaches, including RNA interference (RNAi), improves disease readouts in HD mice models. To advance HTT-targeting RNAi to the clinic we designed an RNAi construct, HDS1 with robust on-target silencing efficacy and minimized silencing of unintended human transcripts (McBride et al., Mol Ther. December 2011; 19(12): 2152-2162). In Rhesus macaques, AAV.miHDS1 delivery to the putamen reduced HTT expression with no adverse effects on neurological status including fine and gross motor skills; no immune activation, and no neuropathology out to 6 weeks post injection. Others showed safety of a different HTT-targeting RNAi in monkeys for 6 months after injection.

Application of HDS1 to HD patients requires further safety testing in rodents, despite the fact that it was optimized for humans. To satisfy this regulatory requirement, we evaluated mice after AAV.miHDS1 injection. In contrast to monkey, neurological deficits occurred acutely in mice brain and could be attributed to off-target silencing through interactions of miHDS1 with the 3' untranslated region of other transcripts. While we resolved miHDS1 toxicity in mouse brain and maintained miHDS1-silencing efficacy, these studies highlight that optimizing nucleic acid-based medicines for safety for human use presents challenges for safety testing in rodents or other distantly related species.

HD is caused by CAG repeat expansion (>36 repeats) within the first exon of huntingtin. Although mutant huntingtin (mHTT) is ubiquitously expressed, the brain, and in particular the striatum, shows robust and earlier degeneration. The incidence of HD is ~5-10 per 100,000 individuals in Europe and USA, with onset generally occurring in the $3^{rd}$ or $4^{th}$ decade of life. To date, management of HD includes drugs that can reduce motor or psychiatric symptoms.

Earlier work using inducible models of HD showed that disease symptoms improve once mHTT expression was turned off, even many weeks post disease onset and after striatal atrophy. This infers that there is a window of opportunity to treat HD after early symptom onset. Thus, methods to reduce gene expression using gene silencing technologies, including RNAi, should be investigated as a therapeutic alternative.

RNAi is an evolutionarily conserved process of post-transcriptional gene silencing by which double stranded small non-coding RNAs (e.g., miRNAs) cause sequence-specific degradation of targeted mRNA sequences. The endogenous RNAi pathway starts with the expression of a larger primary RNA transcript (pri-miRNA) that is sequentially cleaved in the nucleus by Drosha, a component of the microprocessor complex, to generate a precursor miRNA (pre-miRNA). Pre-miRNAs are exported to the cytoplasm and are subsequently cleaved by Dicer to release the mature miRNA. Of the two strands of the miRNA sequence, one (the antisense "guide" strand) is generally preferentially incorporated into the RNA Induced Silencing Complex (RISC), where it will direct binding to the target mRNA and inhibit expression. MiRNAs typically repress mRNA expression through partial complementarity. When one strand of the dsRNA emerging from Dicer cleavage is fully complementary to its target, the resulting small interfering RNA (siRNA) directs endonucleotic cleavage of the target at a base across from nucleotides 10 and 11 of the "guide" strand, triggering mRNA destruction. Scientists have developed different expression based systems to co-opt the endogenous RNAi pathway and suppress the expression of specific genes. For example, RNAi expression systems can be designed to express small hairpin RNA sequences with one of its strands complementary to the targeted mRNA, and enter the pathway at the pre-miRNA (short hairpin RNA; shRNA) or pri-miRNA (artificial miRNA) steps.

For expression systems or siRNAs that are acutely transfected into cells, the active guide strand is designed to be as specific as possible with minimal off-sequence silencing. Off sequence silencing arising from interaction of the guide with other transcripts with full complementarity can be avoided using standard search algorithms. A more difficult type of off-targeting to avoid is that which occurs due to partial complementarity of the RNAi seed sequence, bases 2-7 at the 5' end of the loaded strand, with other mRNA 3'UTR sequences. In this instance, repression of expression occurs via a miRNA-like mechanism. In previous studies, we developed an algorithm, siSPOTR, to design potent RNAi sequences with strong strand biasing for RISC loading, and minimized off-target silencing potential over unintended human transcripts. When siSPOTR was used to design triggers for HTT silencing, we found that miHDS1, expressed from AAV vectors, showed safety at multiple levels following delivery to nonhuman primate putamen.

As a prerequisite for human application, we performed follow up experiments to assess safety in normal rodents. Notably, we found that HDS1 induced robust motor deficits after striatal injections, which could be attributed to unintended silencing of Bcl2. We further show that the off-targeting toxicity could be resolved by several strategies while maintaining HTT-silencing efficacy. Overall these studies highlight the challenge of optimizing nucleic acid based medicines for specificity and safety in humans that when used in distantly related species will portray different, and perhaps disease-inducing, off-targeting profiles.

Results miHDS1 Induces Neurological Deficits in the Mouse Brain

In prior work we designed miHDS1, an artificial miRNA sequence against huntingtin with high on-target silencing efficacy and minimized off-target potential (FIG. 1A). When AAV vectors expressing miHDS1 were injected into the putamen of non-human primates, HTT levels were significantly reduced and there were no signs of neuronal degeneration, immune responses or motor deficits. Overall, these studies highlighted the potential of miHDS1 for HD therapeutics. However, as a pre-requisite for human application, further testing in another species, such as rodents, is required. Thus we set out to perform safety testing of AAV.miHSD1 in normal mice, despite the fact that it was designed for safety in human cells.

As a first step in building the preclinical construct, we redesigned the AAV.miHSD1 vector to contain a stuffer sequence rather than the eGFP expression cassette, which was used in our earlier studies for visualization of transduced regions. The stuffer sequence was designed to be devoid of enhancer or repressor sequences, splice activators or repressors, and antisense or other noncoding RNAs, and of sufficient size for optimal packaging of the small RNAi expression cassette. The final AAV2/1 vectors expressed miHDS1 or miCt1, a control used earlier in many of our in vivo studies (FIG. 1B).

Wild type mice were weighed and basal rotarod performance assessed at 7 weeks of age prior to distribution of animals into groups of equal abilities (to avoid pre-treatment differences between the groups) AAV.miHDS1 or AAV.miCt1 were injected bilaterally into the striatum at 8 weeks of age with AAVmiHDS1/Stuffer (n=13) and AAVmiCt1/Stuffer (n=11) virus (FIG. 1C,D). As early as 2 months after AAV delivery, mice expressing miHDS1 had significant rotarod deficits and showed decreased latency to fall with respect to control-treated littermates (FIG. 1D). And while all animals gained weight over the course of the study, HDS1-treated mice gained significantly less than miCt1-treated mice (FIG. 1E).

Characterization of miHDS1 Off-Target Genes in the Mouse Brain.

miHDS1 was designed to have minimal off-target silencing of human transcripts, but was not optimized for safety in mouse and we did not, a prior, evaluate the sequence for potential toxicity against mouse transcripts in silico. Although the AAV.miHDS1.eGFP construct used earlier in monkeys showed appropriate strand loading, we next tested the fidelity of the miHDS1.stuffer expression cassette for strand biasing, as either strand, if loaded, could illicit off-target silencing. For this we designed reporter constructs consisting of miHDS1 targets cloned downstream of a luciferase reporter. We found repression from the guide strand, and no repression from the non-guide strand (FIG. 1G). This is in line with our earlier in vitro expression analyses of HDS1.eGFP expression cassettes, and is supported by the fact that we designed the miHDS1 sequence with low 5' end thermodynamic stability to promote proper loading of the guide "antisense" strand into the RISC complex. Thus, the neuronal deficits observed by miHDS1 expression is likely due to the binding of the guide "antisense" strand to the 3'UTR of unintended mRNAs and silencing expression by a miRNA-like mechanism.

Because previous studies demonstrated that most off-target effects are due to seed-mediated binding to other mRNA 3'UTRs, we first identified likely miHDS1 off-targets using a common in silico approach. Many different target prediction programs have been described to identify putative miRNA binding sites, such as the TargetScan (TS) and PITA algorithms. TargetScan predicts biological targets for a specific miRNAs by searching 3'UTR sequences for the presence of 8mer and 7mer sites complementary to the miRNA seed sequence. The algorithm improves target prediction accuracy by prioritizing target sites with compensatory 3' base pairing, local sequence context and strong sequence conservation known to be favorable for miRNA-mediated regulation. Because previous work has shown that seed-mediated off-target effects are species-specific, we used TargetScan to predict targets based on seed sequence complementarity in the mouse 3'UTR transcriptome. The PITA algorithm incorporates target-site accessibility to predict miRNA binding sites. For a given target site PITA determines a ddG score value, the free-energy difference between binding of the miRNA to the target ($dG_{duplex}$) and unpairing the target-site nucleotides ($dG_{open}$). Based on PITA, ddG scores below −10 are more likely to be functional for endogenous miRNA targets, although the threshold for an overexpressed miRNA sequence could be higher (between 0 and −10). Thus, in our approach we used TargetScan to identify all potential seed binding sites, followed by the PITA algorithm to determine the ddG score, and ranked all potential miHDS1 sites. Using our approach against the mouse 3' UTRome, we predict 197 transcripts as potential off-targets for miHDS1, with 170 expressed in the striatum (FIG. 3c). As expected, prediction of miHDS1 off-targets in the orthologous human and rhesus 3'UTRs revealed that the miHDS1 off-targeting in mouse is not conserved.

We identified Bcl2, Sdf4, Smad9, Bmi1, Mett12, Lancl1 and Map2k6 among the top 25th percentile of the off target gene list (FIG. 2a,b). We analyzed striatal samples obtained from mice treated with miCt1 or miHDS1 by Q-PCR for these predicted off-targets and mouse Htt. As expected, mouse Htt expression was significantly reduced (up to 70%) in miHDS1-treated mice with respect to miCt1-treated ones (FIG. 2c). Among the set of off-target transcripts assessed, Bcl2, Sdf4, and Map2k6 were significantly reduced on tissue samples obtained from mice treated with AAV.miHDS1 (FIG. 2c). None of these transcripts were predicted to be affected by miCt1. We confirmed these results using an immortalized mouse neuronal striatal cell line that has a normal Htt allele (SthdhQ7 cells). SthdhQ7 cells were electroporated with plasmids expressing miHDS1, miCt1 or no transcript (contained only the U6 promoter), and 24 hours later transcripts were analyzed by Q-PCR. As observed in mouse brain, Bcl2 expression was reduced in miHDS1 expressing cells, but not those expressing miCt1 or control U6 plasmid treated (FIG. 2d). In contrast, Sdf4 and Map2k6 expression was not reduced by overexpression of miHDS1 (FIG. 2d), suggesting that these genes may not be direct off-targets in vivo, and may reflect indirect effects of Htt suppression over time or off-target suppression in non-neuronal cells; although AAV2/1 transduces primarily neurons. Interestingly, of Smad9 expression was significantly increased in SthdhQ7 cells, and was elevated, though not significantly so, in miHDS1 treated striata (FIG. 2d). Thus, our screen revealed Bcl2 as a potential deleterious off-target of HDS1 in the mice 3' UTRome.

Rescuing miHDS1 for Safety in Mouse Brain.

When a miRNA sequence is loaded into RISC containing a catalytic argonaute protein (Ago2), full binding complementarity between a miRNA and its target sequence is required to mediate endonucleotic mRNA cleavage. However, mismatches produced by single point mutations on the miRNA sequence can be tolerated. Thus, to modify the off-target profile of miHDS1, which is directed primarily by the seed region, we introduced single point mutations that were designed to alter the seed without affecting silencing efficacy (FIG. 3A).

As a first step to identify which seed mutations (i) effectively change the off-target profile, (ii) maintain low overall off-targeting potential and (iii) silence human HTT, we repeated the off-target prediction analysis using all single nucleotide seed variants (positions 2-7) of miHDS1 (FIG. 3C). Position 8 mutants were discarded, because the off-target profile extensively overlapped that of miHDS1. This was expected, since position 8 pairing is not necessary for miRNA-mediated silencing. Seed mutants at positions 3 and 4 were also discarded, since these mutations significantly increased the number of predicted off-targets. For the remaining seed variants, overall off-targeting potential was comparable to miHDS1, with less than 10% of miHDS1 off-targets being shared with miHDS1 variants (FIG. 3C)

Thus, we introduced single point mutations at positions 2, 5, 6 and 7 of the miHDS1 seed region to generate the miHDS1 variants. Because our goal is silencing of human HTT, we first screened all the variants in human-derived HEK293 cell line and determined silencing efficacy by Q-PCR (FIG. 4A). Not all miHDS1-variants reduced HTT expression equivalent to the original miHDS1. Compared to miHDS1, mHDS1 variants with mismatches at positions 2 and 7 disrupt miHDS1-silencing efficacy. However, no significant differences were observed for miHDS1-variants containing a mismatch at position 5 or 6. Of note, among the different miHDS1 variants with a mismatch at position 7 only the variant with a C>U substitution had equivalent silencing efficacy than miHDS1, probably due to the thermodynamic stability of the G:U wobble. We choose miHDS1v6A and miHDS1v5U for further experiments based on: (1) its higher silencing efficacy with respect to the other miRNA variants containing a mismatch at the same seed position, and (2) the nucleotide mismatch type generated (U:U, miHDS1v5U; A:G, miHDS1v6A, FIG. 4D) which have a moderate off target profile that differs extensively from HDS1 (FIGS. 4B, 4C, 4E, 4F).

```
The RISC loaded miRNA sequences are the following
(NOTE: 3' → 5'):
                                             (SEQ ID NO: 6)
miHDS1v5U: 3'-CACGACCGAGCGUACCUGCUG-5'

(SEQ ID NO: 7)
miHDS1v6A: 3'-CACGACCGAGCGUACAAGCUG-5'

The Pri-miHDS1 are the following (5' → 3'):
Pri-miHDS1v5U (SEQ ID NO: 8):
NNNAGCGAUGCUGGCUCGCAUGGUCGAUACUGUAAAGCCACAGAUGCUGU

CGUCCAUGCGAGCCAGCACCGCANNN

Pri-miHDS1v6A (SEQ ID NO: 9):
NNNAGCGAUGCUGGCUCGCAUGGUCGAUACUGUAAAGCCACAGAUGCUGU

CGAACAUGCGAGCCAGCACCGCANNN
```

-continued

The Pre-miHDS1 are the following (5' → 3'):
Pre-miHDS1v5U (SEQ ID NO: 10):
5'P-

GCUGGCUCGCAUGGUCGAUACUGUAAAGCCACAGAUGCUGUCGU̲CCAUGC

GAGCCAGCAC-OH3'

Pre-miHDS1v6A (SEQ ID NO: 11):
5'P-

GCUGGCUCGCAUGGUCGAUACUGUAAAGCCACAGAUGCUGUCGA̲ACAUGC

GAGCCAGCAC-OH3'

As expected, expression miHDS1v6A and miHDS1v5U reduced Htt protein levels in both mouse (SthdhQ7) and human (HEK293) cell line, with no significant differences to miHDS1 (FIGS. 4A-4E).

Next, we evaluated the effect of miHDS1v6A and miHDS1v5U over the validated miHDS1 off-target mouse transcripts. Seed pairing stability (SPS), the free energy binding between a miRNA seed and its target mRNA, influences whether a miRNA sequence produces off target silencing effects. Although the miHDS1 variants had a similar SPS value than the original miHDS1 for its own targets, mismatches in the seed region of miHDS1 variants decreased the SPS value over miHDS1 off targets (FIG. 3b). Based on PITA, the introduction of a mismatch in the seed region reduced the ddG score value on all HDS1 predicted off target genes, being more significant for miHDS1v6A than miHDS1v5U. Interestingly, the seed sequence of the miHDS1-variants generated a different target site on some of the same miHDS1 off-target.

We previously demonstrate silencing of Bcl2 in vivo and in vitro by miHDS1. Based on TargetScan, miHDS1v6A and miHDS1v5U will no longer target the Bcl2 3'UTR, and PITA predicts a reduced ddG score at the miHDS1 site, suggesting that Bcl2 silencing will be weakened by miHDS1 v6A or miHDS1 v5U. To test this, SthdhQ7 cells were electroporated with plasmids containing the miRNA expression cassettes or the U6 promoter only control plasmid, and 24 hours later Bcl2, Htt and Smad9 expression was determined by Q-PCR. Relative to controls (miCt1 and U6), Htt mRNA levels were significantly reduced in both miHDS1 and miHDS1-variant electroporated cells (FIG. 4g). But importantly, whereas miHDS1 significantly reduced Bcl2 expression by 40%, no silencing was observed after electroporation of miHDS1v6A. miHDS1v5U expression was still active against Bcl2, retaining silencing levels to 20% (FIG. 4h). Interestingly, Smad9 overexpression associated with miHDS1 expression was not observed in miHDS1v5U or miHDS1v6 electroporated cells (FIG. 4i).

Redirecting miCt1 Against Human Huntingtin mRNA.

Our previous experiments exposed the toxicity of miHDS1 due to its off target effects, but also highlighted that miCt1 is tolerable when expressed in the mouse brain. MiCt1 was designed with a low off-target silencing profile, but was not intended to target the huntingtin mRNA. Therefore, we tested if we could take advantage of the relative safety of the miCtr1 seed in mouse striata, and design a HTT-targeting RNAi trigger around that seed.

As a first step, we screened the human HTT mRNA, or clinical target, for sequences fully complementary to the miCt1 seed region, but found none. Following the same strategy for designing miHDS1 variants, we repeated this in silico analysis allowing single mismatches between nucleotides 2 to 7 of the miRNA sequence. We found four complementary sequences (miHDss1-4): MiHDss1 (mismatch at position 7) and miHDss4 (mismatch at position 4) target HTT in the 3'UTR, whereas miHDss2 (mismatch at position 6) and miHDss3 (mismatch at position 5) target HTT in the coding region spanning the exon7-8 juncture or in exon33, respectively (FIG. 5a,b). When tested in HEK 293 cells, only miHDss3 silenced HTT expression to 40-50% of control-treated cells, as determined by Q-PCR (FIG. 5c) and western blot (FIG. 5d,e).

Because miCt1 and miHDSS3 share the same seed sequence we expect that both miRNAs will have the same off target profile. However, as observed on endogenous miRNAs from a specific miRNA family, silencing efficacy might change because of sequence differences on the 3' region of each miRNA. We used the PITA algorithm to compare miRNA binding stability and silencing potential between miCt1 and miHDss3 off-targets. By our in silico approach we predict 89 off target sites for both miCt1 and miHDss3, with 67 expressed in striatum. Interestingly, the 3' region of miHDss3 increases off target-miRNA binding stability with respect to miCt1 (FIG. 5f).

Characterization of miHDS1 Variants and miHDss3 Tolerability in the Mouse Brain.

To determine the in vivo tolerability of the new sequences, the miRNA expression cassettes were cloned into our AAV shuttle vector (FIG. 6b). Seven weeks old wild type mice were divided into groups based on equivalent weight and basal rotarod performance, and subsequently injected bilaterally in the striatum with virus expressing miHDS1v6A, miHDS1v5U, miHDss3, or miHDS1, miCt1, and Formulation buffer (FB) as experimental controls. Two and four months after injection mouse weight was recorded, and neurologic adverse effects were determined by using the accelerated rotarod, clasping, and open field tests (FIG. 6a).

Consistent with our previous results, mice expressing miHDS1 showed motor deficits on the accelerated rotarod apparatus (FIG. 6c). Also, no differences were observed between mice injected with FB buffer alone or miCt1. This result is important because it suggest the adverse effects are not a result of co-opting the endogenous pathway, but to specific miHDS1 off-target effects. Interestingly, and consistent with our in vitro studies, miHDS1v5U showed rotarod deficits as well. This may reflect that pyrimidine: pyrimidine mismatches (U:U, miRNA:mRNA) display moderate discrimination power and this variant still partially silenced Bcl2 (FIG. 4H). Also predicted from our in vitro work, miHDS1v6A improved miHDS1-mediated toxicity, with no significant differences observed between miHDS1v6A and miCt1 at 2 or 4 month after AAV injection. Besides silencing human huntingtin, miHDss3 shares the same off-target profile than miCt1. However, the PITA algorithm suggested miHDss3 is more prone to silence the miCt1 off-target repertoire by increasing binding stability of the miRNA:mRNA pair (FIG. 5f). However, no significant differences were observed on the accelerating rotarod at 2 or 4 months (FIG. 6c).

With the exception of mice injected with miHDS1v5U that lost weight over time (−1.7 g, 8% reduction at 4 month), body weight gain was recorded in all other groups. Also, weight gain was significantly reduced with miHDS1 treatment, as before. At 4 months, miHDS I-injected mice had 1.3 grams (5%) of body weight gain whereas the other groups had weight increases from 3.6 and 5.2 grams (15-22% increase at 4 month) (FIG. 6d).

Discussion

In this work we set out to test the safety in normal mice of an RNAi trigger designed for safety in humans and shown in earlier work to be safe in nonhuman primates. Testing drugs for human use in two species, generally a rodent and a larger mammal, is standard procedure for regulatory approval to move forward to early phase studies. While we found no notable toxicity in monkeys, which was also reported by others in a later study, when the intended construct was tested in rodents, acute toxicity was noted.

We found that we could reduce the toxicity of the sequence tested, miHDS1, by making point mutations in the seed to alter the off-target profile. Single seed sequence modification changed off-target profile of original miHDS1, while maintaining silencing efficacy. miHDS1v6, but not miHDS1v5, restored miHDS1 tolerability in the mouse brain. miHDS1v5U generated a U:U mismatch, which is a pyrimidine:pyrimidine mismatch, whereas miHDS1v6A generated a A:G which is a Purine:Pyrimidine mismatch, and was found to be the most effective to discriminate.

As an alternative to altering the seed of HDS1, we noted earlier that our control sequence, also designed for low off-targeting potential, could be re-engineered to target human HTT. Both sequences, when tested in mice, were well tolerated and did not induce neuropathology or neurological deficits, as was noted earlier for the parent HDS1.

These findings highlight the contrast between traditional drug development and the newly emerging field of nuclei acid based medicines. While the goal of all human drug development is safety and efficacy in the target population, in the case of nucleic acid based medicines the intended drug interacts directly with the genome and/or the transcripts expressed. Thus, drugs that rely on sequence specificity and optimized for safety in humans will likely interact differently with the genomes of other species, and in particular those of distantly related species such as rodents. On the other hand, if sequences are optimized for safety in rodents, the risk for problems in the context of the human genome is greater.

Summary

The present results highlight (1) safety and tolerability profile of a miRNA is species specific, emphasizing the careful interpretation of initial studies using mouse models of disease, and (2) Single seed sequence modification is an effective strategy to resolve off-target toxicity of a miRNA sequence, while maintaining silencing efficacy.

Material and Methods

Cell Lines and Transfections.

HEK293 were obtained from ATCC and cultured under conditions provided by manufacturer. SthdhQ7 were kindly obtained from Marcy MacDonald. All plasmid DNA transfections on HEK293 were done with lipofectamine 2000 (Invitrogen) using guidelines provided by manufacturer. DNA transfection of SthdhQ7 cells were done using a Invitrogen Neon transfection system using the electroporation conditions and following the guidelines provide by manufacturer.

Vector Design and AAV Production.

Artificial miRNA sequences (miCt1, miHDss variants, miHDS1 and miHDS1 variants were generated by polymerase extension of overlapping DNA oligonucleotides (IDT, Coralville). Polymerase-extended products were purified using Qiaquick PCR purification kit, digested with XhoI-SpeI and cloned into a XhoI-XbaI site on a Pol-III expression cassette containing the mouse U6 promoter, MCS and Pol-III-terminator (6T's).

RNAi luciferase reporter vectors were constructed using psiCheck2 vector (Promega). Tailed DNA oligonucleotides containing a single, perfect complementary RNAi target site for miHDS1 sense or antisense strand were annealed and cloned into XhoI-NotI sites downstream of the stop codon of the Renilla luciferase cDNA sequence.

For in vivo studies, miRNAs expression cassettes were moved into an AAV shuttle plasmid upstream of a DNA stuffer sequence. The miRNA expression cassette and stuffer sequence were flanked at each end by AAV serotype 2 145-bp inverted terminal repeat sequences.

In Vitro Luciferase Assays.

HEK293 cells at 70% confluence grown in a 24-well plate were co-transfected with miRNA-expressing plasmid and RNAi luciferase reporter plasmid. At 24 hrs, cells were rinsed with ice-cold PBS and Renilla and Firefly luciferase activities were assessed using the Dual-Luciferase Reporter Assay System (Promega) according to the manufacturer's instructions, using 20 µl of cell lysate. Luminescent readouts were obtained with a Monolight 3010 luminometer (Pharmigen, USA). Relative light units were calculated as the quotient of Renilla/Firefly relative light units and results expressed relative to a control miRNA.

Western Blot Analysis.

HEK293 cells were transfected with miRNA expressing cassettes as indicated. At 48 hours cells were rinsed once with iced-cold PBS and lysed with Passive lysis buffer (PBL, Promega). Protein concentration was determined by the Bradford-Lowry method (BioRad) and 10 µg of protein loaded on a NuPAGE 3-8% Tris-Acetate gel (Novex Life technologies). Proteins were transferred onto PVDF membranes and incubated with a mouse anti-Htt (1:5000, Millipore, Calif.), or rabbit anti Beta-actin (1:40000, Sigma) antibodies followed by horseradish peroxidase-coupled antibodies (1:10,000, mouse; or 1:50,000, Rabbit; Jackson ImmunoResearch, West Grove, Pa.). Blots were developed with ECL-Plus reagents (Amersham Pharmacia). Silencing efficacy was determined by densitometry (n=4 independent experiments) of protein levels relative to beta actin with the VersaDoc™ Imaging System (Biorad) and Quantity OneR analysis software.

RNA Extraction and QPCR Analysis.

Total RNA isolation was extracted using Trizol (Life Technologies, Grand Island, N.Y.) according to the manufacturer's protocol, with the exception of 1 µl Glycoblue addition to the aqueous phase on the isopropanol precipitation step and a single wash with cold 70% Ethanol. RNA samples were quantified by spectrophotometry and subsequently cDNAs generated from 500 ng of total RNA with random hexamers (TaqMan RT reagents, Applied Biosystems). SyBrGreen Q-PCR primers pairs for mouse off target genes were designed using the RealTime PCR Custom Assay Design webserver (IDT, Coralville). A seven-point standard curve with a final melting curve assay was performed to validate each primer pair. Only primers pairs with amplification efficiencies of a 100±5% and a single amplification product were used to determine relative gene expression using the ddCt method.

Mouse Studies

All animal protocols were approved by the University of Iowa Animal Care and Use Committee. Wild-type FBV and BACHD mice were obtained from Jackson Laboratories (Bar Harbor, Me., USA). Mice were genotyped using primers specific for the mutant human huntingtin transgene flanking the CAG repeat, and transgenic and age-matched wild-type littermates were used for the indicated experiments. Mice were housed in a temperature-controlled environment on a 12-h light/dark cycle. Food and water were provided ad libitum. At the indicated times mice were injected with AAV2/1-mU6-miRNA/Stuffer virus. For AAV injections, mice were anesthetized with a ketamine and xylazine mix, and 5 l of AAV were injected bilaterally into striatum at a rate of 0.2 µl/min (coordinates: +0.86 mm rostral to Bregma, +/−1.8 mm lateral to medial, −2.5 mm ventral from brain surface). Mice used for gene expression analyses were anesthetized with a ketamine and xylazine mix and perfused with 18 ml of 0.9% cold saline mixed with 2 ml of RNAlater (Ambion) solution. At the indicated times mice were sacrificed and the brain was removed, blocked, and cut into 1-mm-thick coronal slices. Tissue punches from striatum were taken by using a tissue corer (1.4-mm in diameter; Zivic Instruments, Pittsburgh, Pa., USA). All tissue punches were flash frozen in liquid nitrogen and stored at −80 C until used.

Behavior Analysis

Motor coordination of injected mice was determined using the Rotarod apparatus (model 47,600; Ugo Basile, Comerio, Italy). A basal rotarod test was performed at 7 weeks of age and again 2 and 4 months after AAV injection. Mice were tested for four consecutive days with three trials per day, with a 30 min period of rest between trials and a 5-minute habituation period each day beginning sixty minutes before the first trial. The latency to fall per mouse was calculated by averaging the best two trials of each mouse per day of the four consecutive days tested. For the clasping test each mouse was suspended by the tail for one minute and scored as clasping if the mouse held its front paws together near its torso.

All publications, patents and patent applications are incorporated herein by reference. While in the foregoing specification this invention has been described in relation to certain preferred embodiments thereof and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A nucleic acid encoding an artificial primary miRNA transcript (pri-miRNA) consisting of, in order of position, a 5'-flanking region, a non-guide region, a loop region, a guide region, and a 3'-flanking region, wherein the guide region consists of SEQ ID NO: 37 (miHDss3), SEQ ID NO:6 (miHDS1v5U) or SEQ ID NO:7 (miHDS1v6A), and the non-guide region is at least 80% complementary to the guide region.

2. The nucleic acid of claim 1, wherein the 5'-flanking region comprises a 5'-joining sequence contiguously linked to the non-guide region.

3. The nucleic acid of claim 2, wherein the 5'-joining sequence consists of 5-8 nucleotides.

4. The nucleic acid of claim 2, wherein the 5'-joining sequence encodes GUGAGCGA (SEQ ID NO:13) or GUGAGCGC (SEQ ID NO:14).

5. The nucleic acid of claim 2, wherein the 5'-flanking region further comprises a 5'-bulge sequence positioned upstream from the 5' joining sequence.

6. The nucleic acid of claim 2, wherein the 3'-flanking region comprises a 3' joining sequence contiguously linked to the guide region, and wherein the 3'-joining sequence is at least 85% complementary to the 5'-joining sequence.

7. The nucleic acid of claim 5, wherein the 5'-bulge sequence comprises a cloning site.

8. The nucleic acid of claim 5, wherein the 5'-bulge sequence consists of about 1-10 nucleotides.

9. The nucleic acid of claim 5, wherein the 5'-bulge sequence encodes UAAACUCGA (SEQ ID NO:15).

10. The nucleic acid of claim 5, wherein the 5'-flanking region further comprises a 5'-spacer sequence positioned upstream from the 5'-bulge sequence.

11. The nucleic acid of claim 5, wherein the 3'-flanking region comprises a 3' joining sequence contiguously linked to the guide region, wherein the 3'-flanking region further comprises a 3'-bulge sequence positioned downstream from the 3'-joining sequence, and wherein the 5'-bulge sequence is complementary to the 3'-bulge sequence at only one nucleotide at each end of the 5'-bulge sequence.

12. The nucleic acid of claim 10, wherein the 5'-spacer sequence consists of 10-12 nucleotides.

13. The nucleic acid of claim 10, wherein the 5'-spacer sequence encodes UGGUACCGUU (SEQ ID NO:16).

14. The nucleic acid of claim 10, wherein the 5'-flanking region further comprises a 5'-upstream sequence positioned upstream from the 5'-spacer sequence.

15. The nucleic acid of claim 10, wherein the 3'-flanking region comprises a 3'-joining sequence contiguously linked to the guide region, wherein the 3'-flanking region further comprises a 3'-bulge sequence positioned downstream from the 3'-joining sequence, wherein the 3'-flanking region further comprises a 3'-spacer sequence positioned downstream from the 3'-bulge sequence, and wherein the 3'-spacer sequence is at least 70% complementary to the 5'-spacer sequence.

16. The nucleic acid of claim 14, wherein the 5'-upstream sequence is about 30-2000 nucleotides in length.

17. The nucleic acid of claim 14, wherein the 3'-flanking region comprises a 3'-joining sequence contiguously linked to the guide region, wherein the 3'-flanking region further comprises a 3'-bulge sequence positioned downstream from the 3'-joining sequence, wherein the 3'-flanking region further comprises a 3'-spacer sequence positioned downstream from the 3'-bulge sequence, wherein the 3'-flanking region further comprises a 3'-downstream sequence positioned downstream from the 3'-spacer sequence, and wherein the 5'-upstream sequence is less than 20% homologous to the 3'-downstream sequence.

18. The nucleic acid of claim 1, wherein the 3'-flanking region comprises a 3'-joining sequence contiguously linked to the guide region.

19. The nucleic acid of claim 18, wherein the 3'-joining sequence consists of 5-8 nucleotides.

20. The nucleic acid of claim 18, wherein the 3'-joining sequence encodes CGCCUAC (SEQ ID NO:18).

21. The nucleic acid of claim 18, wherein the 3'-flanking region further comprises a 3'-bulge sequence positioned downstream from the 3'-joining sequence.

22. The nucleic acid of claim 21, wherein the 3'-bulge sequence comprises a cloning site.

23. The nucleic acid of claim 21, wherein the 3'-bulge sequence consists of about 1-10 nucleotides.

24. The nucleic acid of claim 21, wherein 3'-bulge sequence encodes UAG (SEQ ID NO:30).

25. The nucleic acid of claim 21, wherein the 3'-flanking region further comprises a 3'-spacer sequence positioned downstream from the 3'-bulge sequence.

26. The nucleic acid of claim 25, wherein the 3'-spacer sequence consists of 10-12 nucleotides.

27. The nucleic acid of claim 25, wherein the 3'-spacer sequence encodes AGCGGCCGCCA (SEQ ID NO:19).

28. The nucleic acid of claim 25, wherein the 3'-flanking region further comprises a 3'-downstream sequence positioned downstream from the 3'-spacer sequence.

29. The nucleic acid of claim 28, wherein the 3'-downstream sequence is about 30-2000 nucleotides in length.

30. The nucleic acid of claim 1, wherein the loop region is from 15-25 nucleotides in length.

31. An expression cassette encoding the isolated nucleic acid described in claim 1 operably linked to a promoter.

32. The expression cassette of claim 31, wherein the promoter is a tissue-specific promoter.

33. The expression cassette of claim 31, wherein the promoter is an inducible promoter.

34. A vector comprising the expression cassette of claim 31.

35. The vector of claim 34, wherein the vector is an adeno-associated virus (AAV) vector.

36. The vector of claim 35, wherein the AAV is AAV1, AAV2, AAV5, AAV6 and/or AAV9.

37. The vector of claim 36, wherein the AAV is AAV2.

38. An isolated microRNA molecule comprising the nucleic acid of claim 1 having an overhang at the 3' end.

39. The isolated microRNA molecule of claim 38, wherein the overhang is a 2 to 5-nucleotide repeat.

40. The isolated microRNA of claim 38, wherein the overhang is a UU (SEQ ID NO:24), UUU (SEQ ID NO:25) or UUUU (SEQ ID NO:26) sequence.

41. The isolated microRNA of claim 38, wherein the overhang is a CUU (SEQ ID NO:27), CUUU (SEQ ID NO:28) or CUUUU (SEQ ID NO:29) sequence.

42. An isolated nucleic acid between 80-4000 nucleotides in length, comprising a nucleic acid encoding an artificial primary miRNA transcript (pri-miRNA) consisting of, in order of position, a 5'-flanking region, a non-guide region, a loop region, a guide region, and a 3'-flanking region, wherein the guide region consists of SEQ ID NO: 37 (miHDss3), SEQ ID NO:6 (miHDS1v5U) or SEQ ID NO:7 (miHDS1v6A), and the non-guide region is at least 80% complementary to the guide region.

43. An isolated nucleic acid consisting of Pri-miHDS1v5U (SEQ ID NO:8), Pri-miHDS1v6A (SEQ ID NO:9), Pre-miHDS1v5U (SEQ ID NO:10), or Pre-miHDS1v6A (SEQ ID NO:11).

44. An isolated RNA duplex comprising a guide region of nucleic acid and a non-guide region of nucleic acid, wherein the guide region consists of SEQ ID NO: 37 (miHDss3), SEQ ID NO:6 (miHDS1v5U) or SEQ ID NO:7 (miHDS1v6A) and the non-guide region is at least 80% complementary to the guide region.

45. The isolated RNA duplex of claim 44, wherein the duplex is between 19-30 base pairs in length.

46. A method of inducing RNA interference comprising administering to a subject an effective amount of the nucleic acid of claim 1.

47. A method of inducing low-toxicity RNA interference comprising administering to a subject the nucleic acid of claim 1.

48. A method of treating a subject with Huntington's Disease, comprising administering to the subject the nucleic acid of claim 1 so as to treat the Huntington's Disease.

49. The method of claim 46, wherein the nucleic acid is administered to the brain of the subject either directly or via the bloodstream.

50. The method of claim 49, wherein the nucleic acid is administered intra-cranially.

51. The method of claim 50, wherein the nucleic acid is administered to the subject's cisterna magna, striatum, cortex or ventricle, subarachnoid space and/or intrathecal space.

52. The method of claim 49, wherein the subject is human.

53. The method of claim 49, wherein the nucleic acid is injected at 1-5 locations in the CNS.

* * * * *